(12) United States Patent
Brunner et al.

(10) Patent No.: US 12,678,081 B2
(45) Date of Patent: Jul. 14, 2026

(54) SYSTEMS AND METHODS FOR DETECTION OF NEUROPHYSIOLOGICAL SIGNAL OSCILLATIONS

(71) Applicant: Washington University, St. Louis, MO (US)

(72) Inventors: Peter Brunner, St. Louis, MO (US); Hohyun Cho, St. Louis, MO (US)

(73) Assignee: Washington University, St. Louis, MO (US)

( * ) Notice: Subject to any disclaimer, the term of this patent is extended or adjusted under 35 U.S.C. 154(b) by 84 days.

(21) Appl. No.: 18/193,930

(22) Filed: Mar. 31, 2023

(65) Prior Publication Data

US 2024/0074687 A1 Mar. 7, 2024

Related U.S. Application Data

(60) Provisional application No. 63/326,257, filed on Mar. 31, 2022.

(51) Int. Cl.
*A61B 5/242* (2021.01)
*A61B 5/00* (2006.01)
(52) U.S. Cl.
CPC ............ *A61B 5/242* (2021.01); *A61B 5/7225* (2013.01); *A61B 5/7246* (2013.01); *A61B 5/7253* (2013.01); *A61B 5/742* (2013.01)
(58) Field of Classification Search
CPC ..... A61B 5/242; A61B 5/7225; A61B 5/7246; A61B 5/7253; A61B 5/742; A61B 5/374
See application file for complete search history.

(56) References Cited

U.S. PATENT DOCUMENTS

| | | | |
|---|---|---|---|
| 6,370,414 B1* | 4/2002 | Robinson ............... | A61B 5/245 |
| | | | 324/260 |
| 2006/0149160 A1* | 7/2006 | Kofol ..................... | A61B 5/369 |
| | | | 600/544 |
| 2010/0042011 A1* | 2/2010 | Doidge .................. | A61B 5/369 |
| | | | 600/544 |
| 2020/0348287 A1* | 11/2020 | Muotri ............... | G01N 33/5011 |

OTHER PUBLICATIONS

Samuel A Neymotin, Idan Tal et al. Taxonomy of neural oscillation events in primate auditory cortex 2020.04.16.045021; doi: https://doi.org/10.1101/2020.04.16.045021 (Year: 2021).*
Golesorkhi, M., Gomez-Pilar, J., Zilio, F et al. The brain and its time: intrinsic neural timescales are key for input processing. Commun Biol 4, 970 (2021). https://doi.org/10.1038/s42003-021-02483-6 (Year: 2021).*

(Continued)

*Primary Examiner* — Pascal M Bui Pho
*Assistant Examiner* — Nicholas A Robinson
(74) *Attorney, Agent, or Firm* — Armstrong Teasdale LLP

(57) ABSTRACT

Systems and methods for detecting oscillations in neural signals are disclosed that provide for high precision and specificity in detecting neural oscillations in time and frequency domains. The disclosed systems and methods identify oscillations according to criteria including 1/f noise, number of cycles, and auto-correlation. The disclosed method detects periodic signals and filters out spurious oscillations associated with harmonic frequencies.

20 Claims, 38 Drawing Sheets
(32 of 38 Drawing Sheet(s) Filed in Color)

(56)                 References Cited

OTHER PUBLICATIONS

Gyurkovics M, Clements GM, Low KA, Fabiani M, Gratton G. The impact of 1/f activity and baseline correction on the results and interpretation of time-frequency analyses of EEG/MEG data: A cautionary tale. Neuroimage. Aug. 15, 2021;237:118192. doi: 10.1016/j.neuroimage.2021.118192. Epub May 25, 2021. (Year: 2021).*

Gips et al., Discovering recurring patterns in electrophysiological recordings, Journal of Neuroscience Methods, 2017, pp. 66-79, vol. 275.

Chen et al., Real-Time Brain Oscillation Detection and Phase-Locked Stimulation Using Autoregressive Spectral Estimation and Time-Series Forward Prediction, IEEE, 2011.

Donoghue et al., Parameterizing neural power into periodic and aperiodic components, Nature neuroscience, 2020, pp. 1655-1665, vol. 23, No. 12.

Neymotin et al., Taxonomy of neural oscillation events in primate auditory cortex, bioRxiv, 2020, Apr. 2020.

Cole et al., Cycle-by-cycle analysis of neural oscillations, bioRxiv, 2018, 302000.

* cited by examiner

White noise

1/f noise

Time domain

Frequency domain

- 1/f pink noise  Different level

- Single sinusoidal signals
- Multiple sinusoidal signals
- Harmonic signals

Different frequency
Different burst duration

Combined signal

Denoised TF map

Final outputs

Power spectrum

SYSTEMS AND METHODS FOR DETECTION OF NEUROPHYSIOLOGICAL SIGNAL OSCILLATIONS

CROSS-REFERENCE TO RELATED APPLICATIONS

This application claims priority from U.S. Provisional Application Ser. No. 63/326,257 filed on Mar. 31, 2022, which is incorporated herein by reference in its entirety.

STATEMENT REGARDING FEDERALLY SPONSORED RESEARCH OR DEVELOPMENT

This invention was made with government support under EB018783, NS108916, MH109429, NS109103, and EB026439 awarded by the National Institutes of Health and W911NF-07-1-0415, W911NF-14-1-0440, and W911NF-08-1-0216 awarded by the Army Research Office. The government has certain rights in the invention.

MATERIAL INCORPORATED-BY-REFERENCE

Not applicable.

FIELD OF THE DISCLOSURE

The present disclosure generally relates to automatically detecting oscillations within neurophysiological signals.

BACKGROUND OF THE DISCLOSURE

Neural oscillations in the mammalian brain have been extensively studied, with tens of thousands of publications. The reason is that oscillations can reflect various cognitive, perceptual, and behavioral states. Also, neurological and psychiatric disorders can yield abnormal oscillations in the brain.

Traditionally, the presence and frequency of neural oscillations are determined by identifying peaks over 1/f noise within the power spectrum. However, this approach solely operates within the frequency domain (Donoghue et al., Nat. Neurosci., 23, 1655-1665, 2020) and thus can neither accurately determine the oscillation's onset/offset time, nor properly distinguish between the fundamental frequency of a non-sinusoidal oscillation and its harmonics. A variety of oscillation detection methods have been developed to date, but no existing method considers the following three criteria: 1) oscillations (peaks over 1/f noise) must be present in the time and frequency domains; 2) oscillations must exhibit at least two full cycles; and 3) oscillations must share the same periodicity as the original time-series.

The reason for the first criterion is to distinguish periodic and aperiodic components in the power spectrum of neural data. Since aperiodic activity has a 1/f distribution in the power spectrum, flattening the power spectrum by removing the 1/f trend is essential to detect oscillations. Next, the second criterion is asking how many cycles should be considered as an oscillation. In general, event-related potentials (ERP) in brain signals can generate less than 2 cycles of fluctuations. To distinguish ERP and neural oscillations, this criterion is also important. Last, the third criterion is to distinguish between the fundamental frequency of a non-sinusoidal oscillation and its harmonics. In general, neural oscillation has lots of harmonic peaks in the power spectrum, due to the non-sinusoidal shape of the signal. A simple 1/f approach will yield detections of spurious harmonic frequencies. Thus, the third criterion is also in critical need for detecting the fundamental frequency of the oscillation.

Other objects and features will be in part apparent and in part pointed out hereinafter.

SUMMARY OF THE DISCLOSURE

The present disclosure is directed to a method of oscillation detection based on three criteria: 1) oscillations (peaks over 1/f noise) must be present in the time and frequency domains; 2) oscillations must exhibit at least two full cycles; and 3) oscillations must share the same periodicity as the original time-series autocorrelation.

The disclosed method detects neural oscillations with high specificity (low false positive and high true negative detection accuracy) and is suitable for use in a variety of applications related to the analysis of neural oscillations, for example, oscillatory monitoring for sleep stages or depth of anesthesia, mu-rhythm based brain-computer interface (BCI), alpha oscillation based neurofeedback, oscillatory monitoring of mental fatigue level, beta oscillations of the motor cortex in stroke and Parkinson patients, and so on.

The disclosed method includes removing 1/f noise in the time-frequency space, determining the initial onset and offset of oscillations, rejecting those oscillations with less than two cycles, and rejecting any oscillations with frequencies different from the autocorrelation frequency. The analysis of oscillations using the disclosed method yields onset, offset, center frequency, frequency range, number of cycles, and degree of asymmetry for each detected oscillation.

DESCRIPTION OF THE DRAWINGS

The patent or application file contains at least one drawing executed in color. Copies of this patent or patent application publication with color drawing(s) will be provided by the Office upon request and payment of the necessary fee.

Those of skill in the art will understand that the drawings, described below, are for illustrative purposes only. The drawings are not intended to limit the scope of the present teachings in any way.

FIG. 21 contains a series of maps and graphs summarizing the detection and mapping of beta oscillations obtained using the disclosed oscillation detection method in one aspect.

Figure 1:
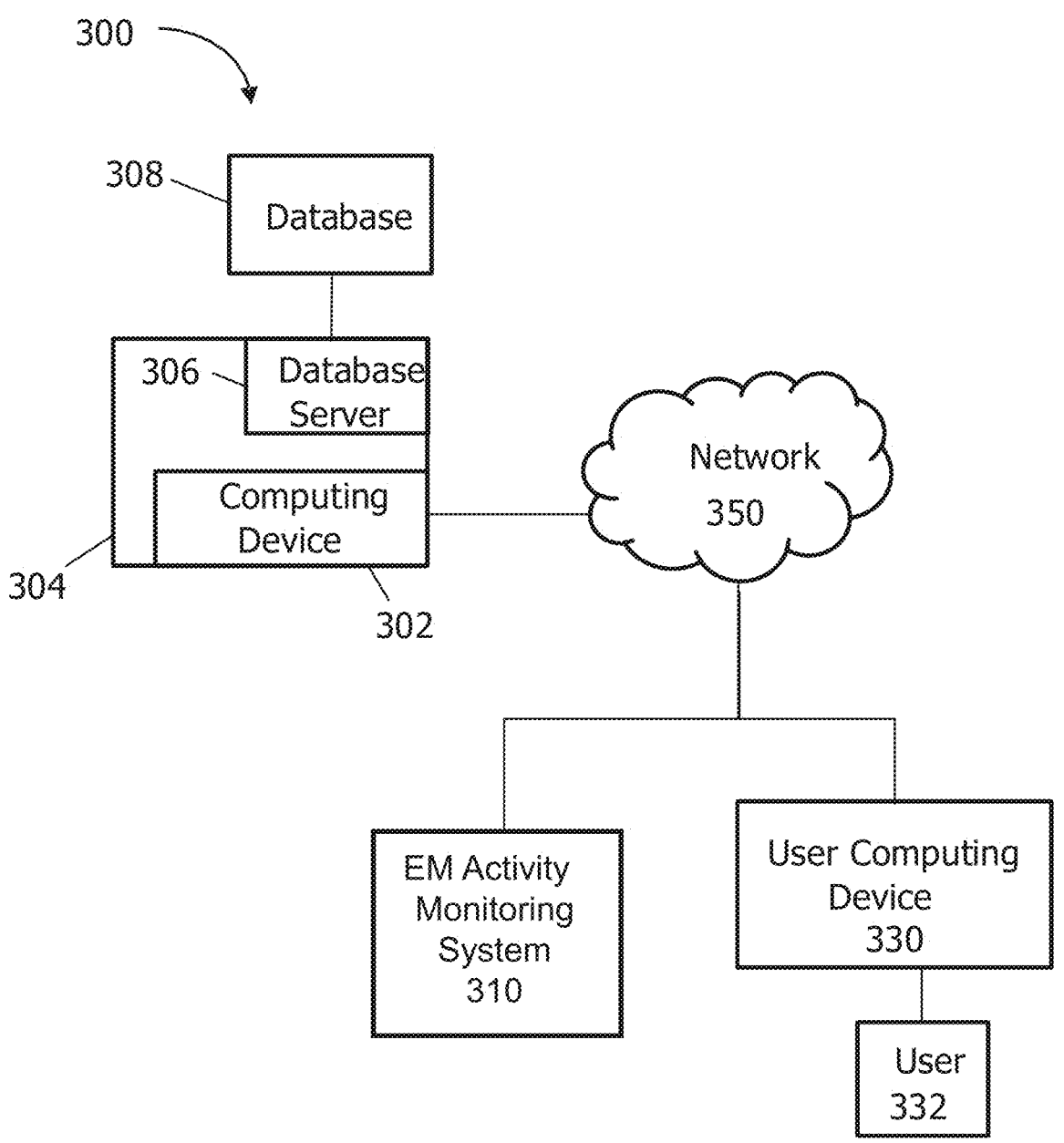
FIG. 1 is a block diagram schematically illustrating a system in accordance with one aspect of the disclosure.

There are shown in the drawings arrangements that are presently discussed, it being understood, however, that the present embodiments are not limited to the precise arrangements and are instrumentalities shown. While multiple embodiments are disclosed, still other embodiments of the present disclosure will become apparent to those skilled in the art from the following detailed description, which shows and describes illustrative aspects of the disclosure. As will be realized, the invention is capable of modifications in various aspects, all without departing from the spirit and scope of the present disclosure. Accordingly, the drawings and detailed description are to be regarded as illustrative in nature and not restrictive.

DETAILED DESCRIPTION

In various aspects, systems, and methods of detecting oscillations within neurophysiological signals are disclosed. The disclosed methods may be used to detect oscillations within any suitable neurophysiological signal or neural signal without limitation. Non-limiting examples of suitable neurophysiological signals or neural signals suitable for analysis using the systems and methods disclosed herein include electroencephalography (EEG) signals, magnetoencephalography (MEG) signals, electrocorticography (ECoG) signals, stereo EEG (sEEG) signals, single neuronal recordings, and local field potentials (LFP). As used herein, the term "neurophysiological signal or neural signal" refers broadly to any signal reflecting the electromagnetic (EM) activity of the brain.

As used herein, the term "oscillation" refers to rhythmic or repetitive patterns of neural activity in the central nervous system. non-limiting examples of oscillations suitable for identification using the systems and methods disclosed herein include, such as delta (<4 Hz), theta (4-8 Hz), alpha (8-12 Hz), beta (13-30 Hz), and low gamma (30-70 Hz) band oscillations.

Figure 5:
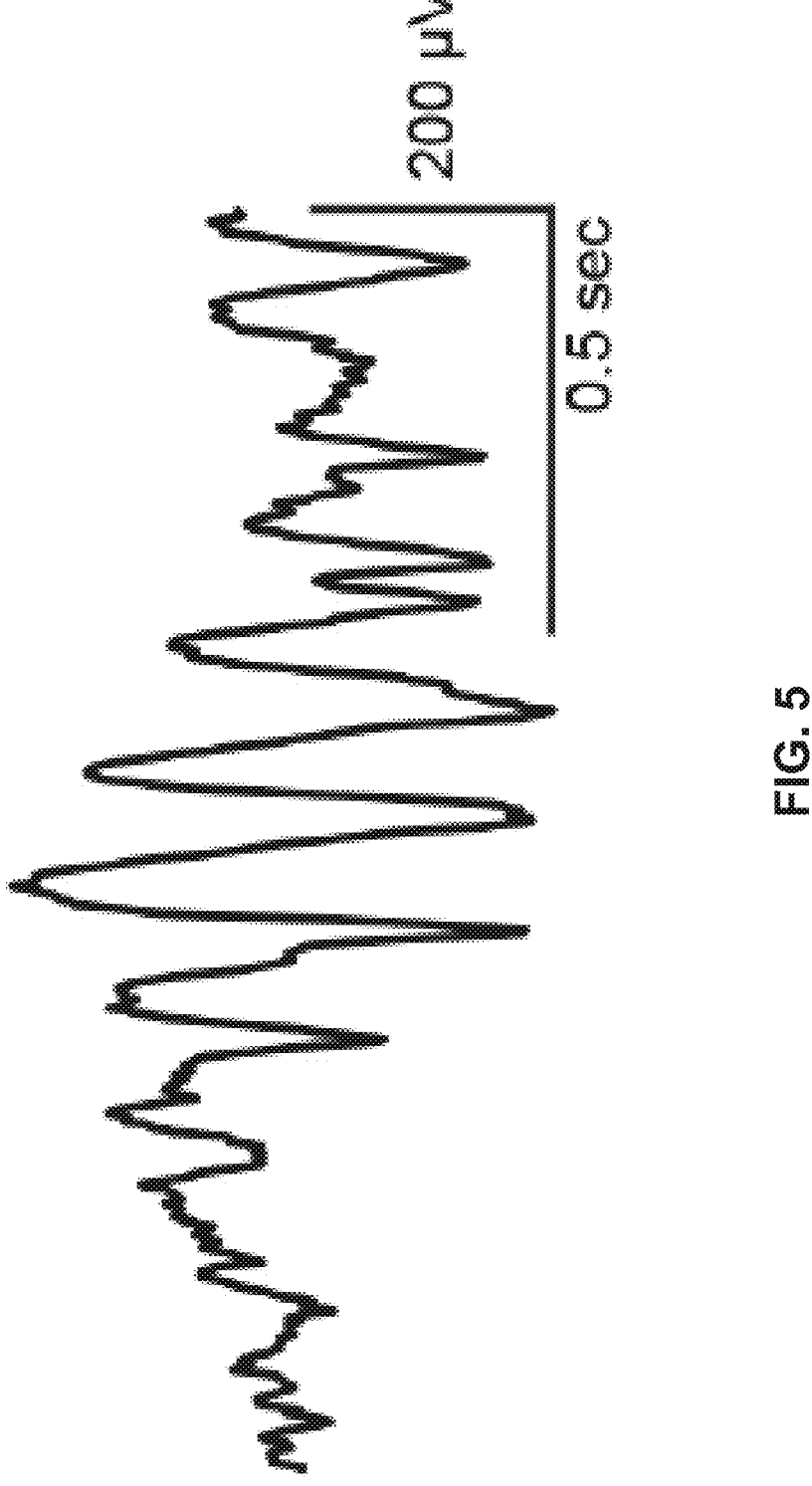
FIG. 5 is a schematic diagram showing an exemplary electrocorticographic (ECoG) signal from the audio cortex.
Figure 6:
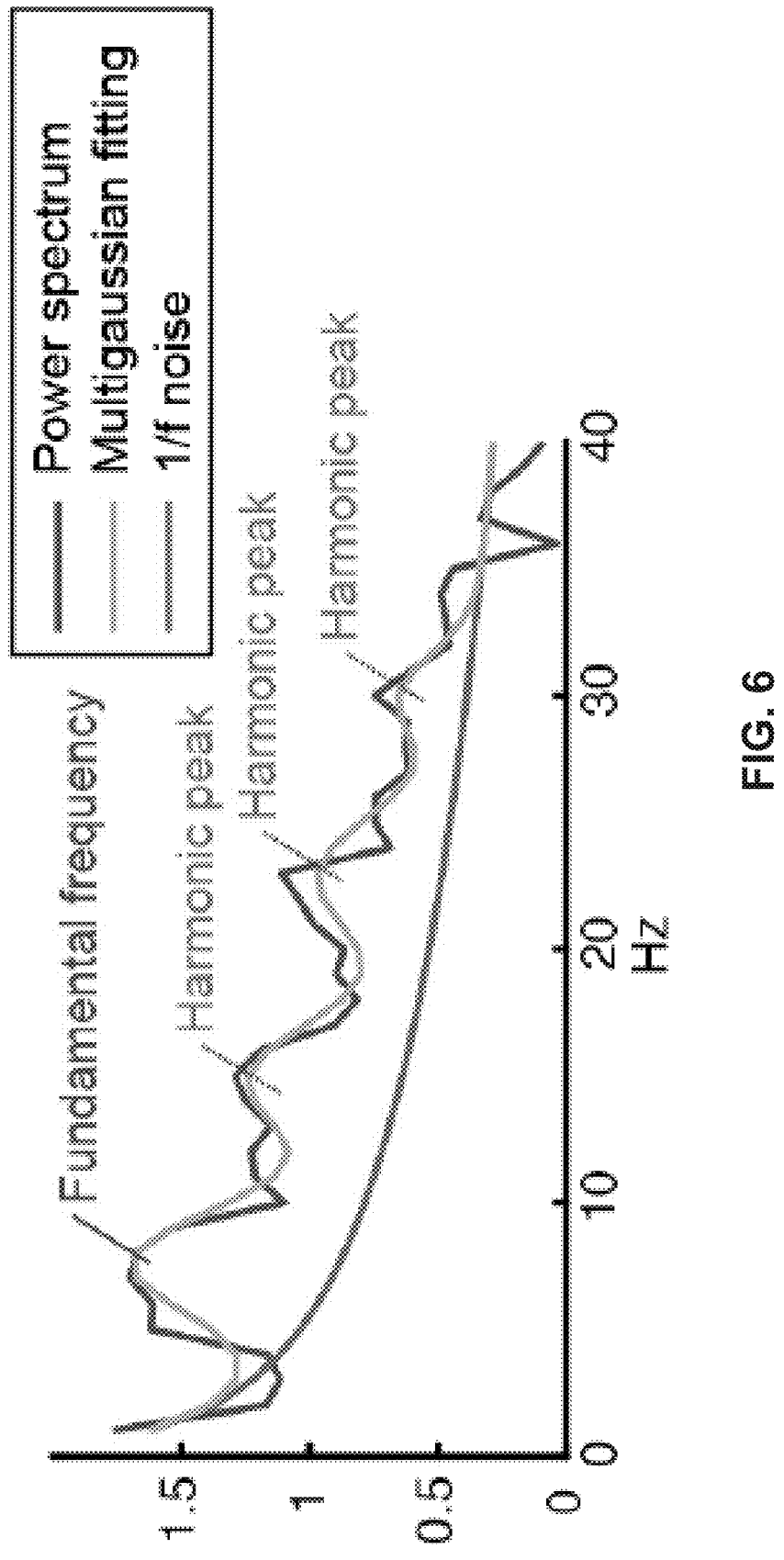
FIG. 6 is a graph showing an exemplary power spectrum acquired from the time-based ECoG signal of FIG. 5, showing that the non-sinusoidal oscillation has multiple harmonic peaks.

As illustrated in FIGS. 5 and 6, detecting the temporal and frequency features of non-sinusoidal oscillations (FIG. 5) is challenging because the power spectrum (FIG. 6) of the non-sinusoidal oscillation may contain multiple harmonic peaks. For example, the effects of broadband shifts and exponent change in power spectra can have the same cumulative effect on changes in spectral power, so they cannot be differentiated. Further, there can also be a tradeoff between spectral and temporal accuracy in oscillation detection.

Figure 16:
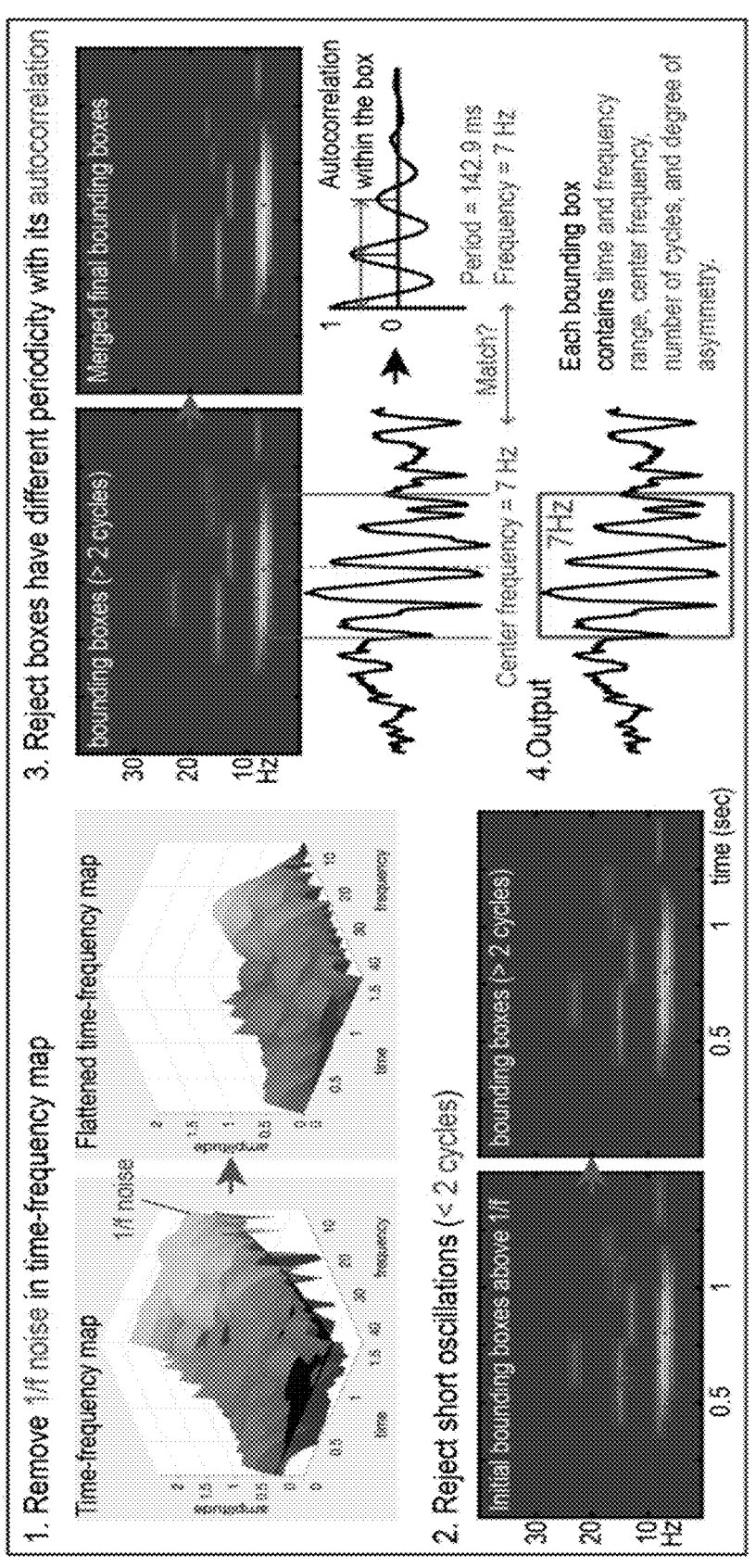
FIG. 16 is a schematic overview of the disclosed oscillation detection method in one aspect.
Figure 17:
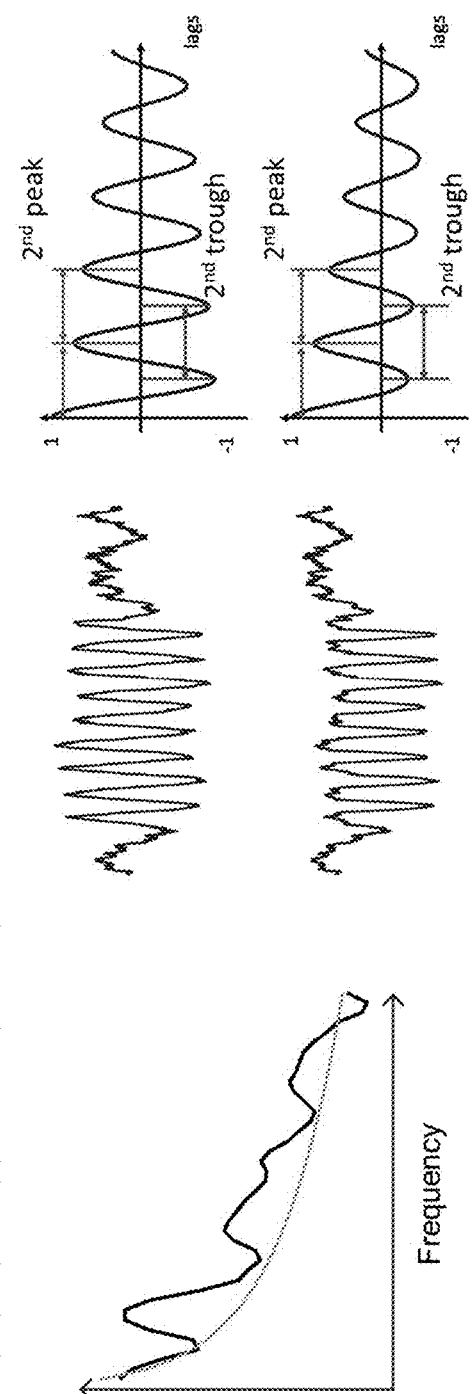
FIG. 17 is a schematic overview illustrating the criteria used for the identification of neural oscillations using the disclosed oscillation detection method in one aspect.

FIG. 16 is a schematic diagram that provides an overview of the oscillation detection method in one aspect. The method includes receiving, obtaining, or providing neurophysiological signal data containing at least one time series of EM measurements indicative of electromagnetic (EM) activity of the brain. As illustrated in FIG. 17, the method includes identifying oscillations within each time series of EM measurements based on three criteria. In one aspect, neural oscillations identified according to the disclosed method contribute to spectral power in excess of 1/f pink noise (see lower left spectrum). In another aspect, the neural oscillations identified according to the disclosed method include at least two oscillation cycles. In another additional aspect, the neural oscillations identified according to the disclosed method are autocorrelated within the raw time series of EM measurements.

Figures 7A, 7B:
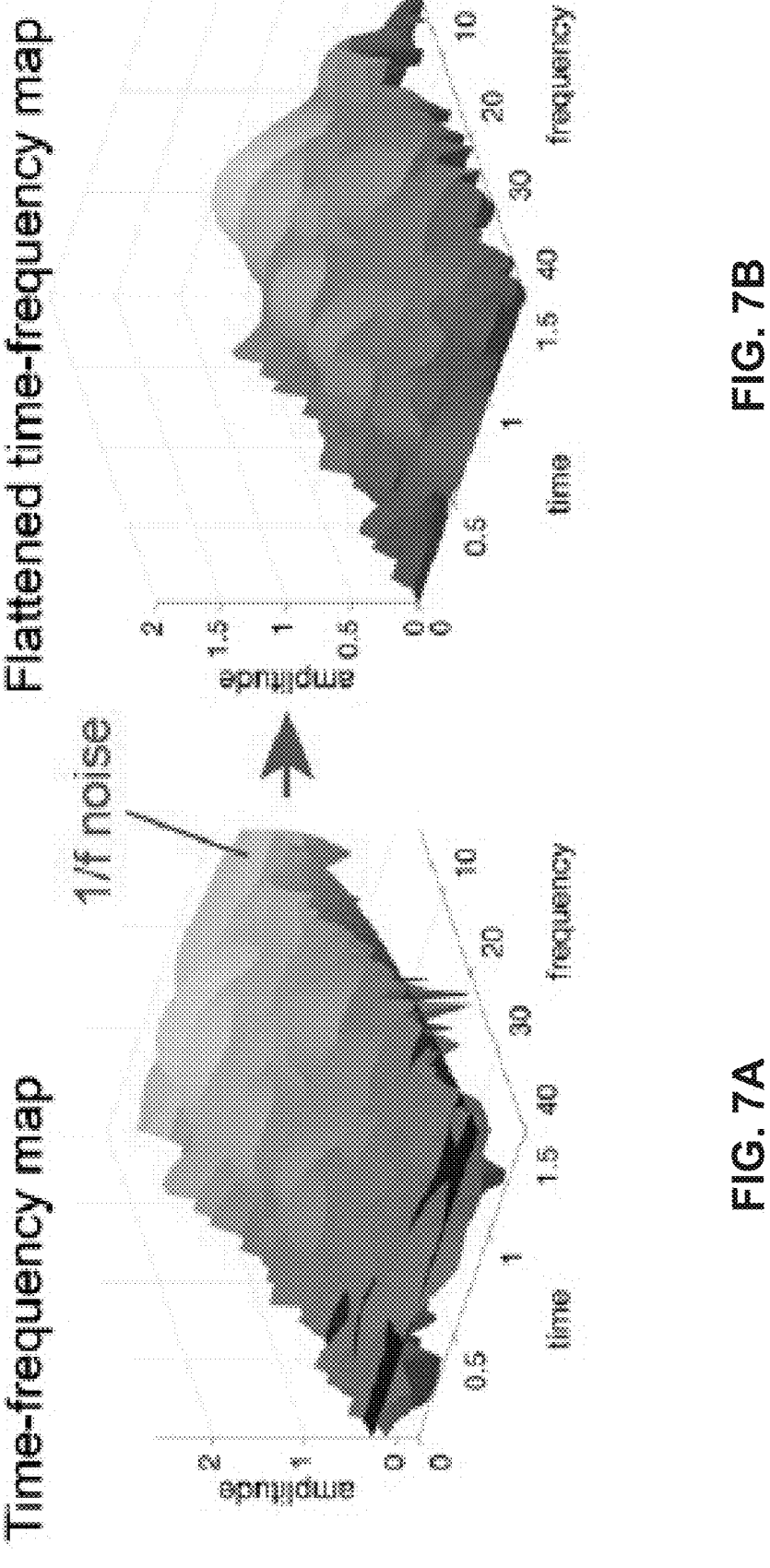
FIG. 7A is a graph showing an exemplary time-frequency map that is transformed by the disclosed oscillation detection method in one aspect.
FIG. 7B is a graph showing a flattened time-frequency map acquired from the graph of FIG. 7A by removing 1/f noise in the time-frequency space.
Figure 18:
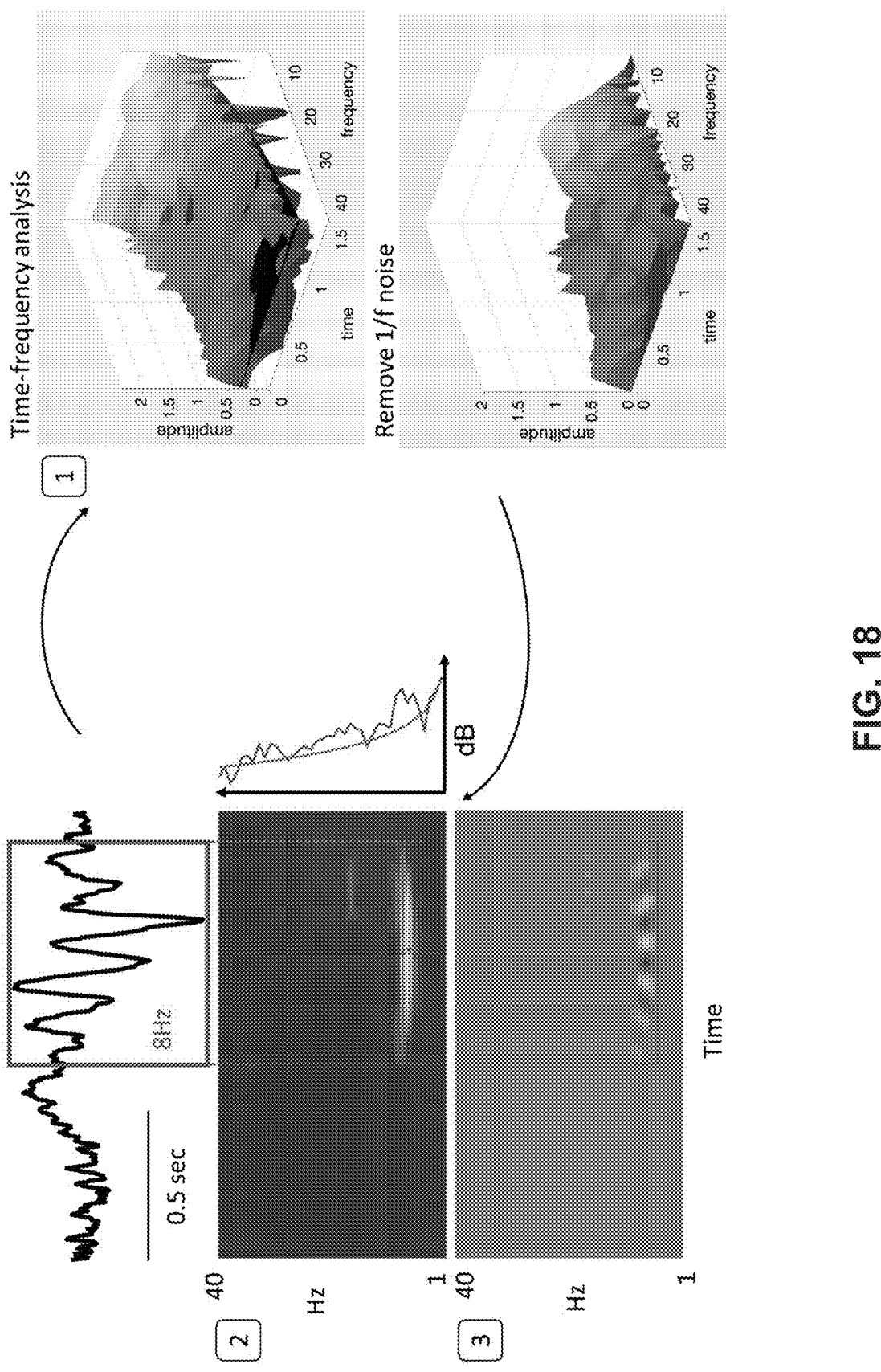
FIG. 18 is a schematic overview illustrating a time-frequency analysis used by the disclosed oscillation detection method in one aspect.

As illustrated in FIG. 18, the disclosed oscillation method includes transforming each raw time series of EM measurements into the time-frequency space to produce a time-frequency map 1 (see also FIG. 7A). In the time-frequency space, the 1/f pink noise is removed from the EM data to produce a flattened time-frequency map, shown also in FIG. 7B. This 1/f noise approach provides thresholds throughout the time-frequency space to identify potential detect periodic signals for each frequency point.

Figures 8A, 8B:
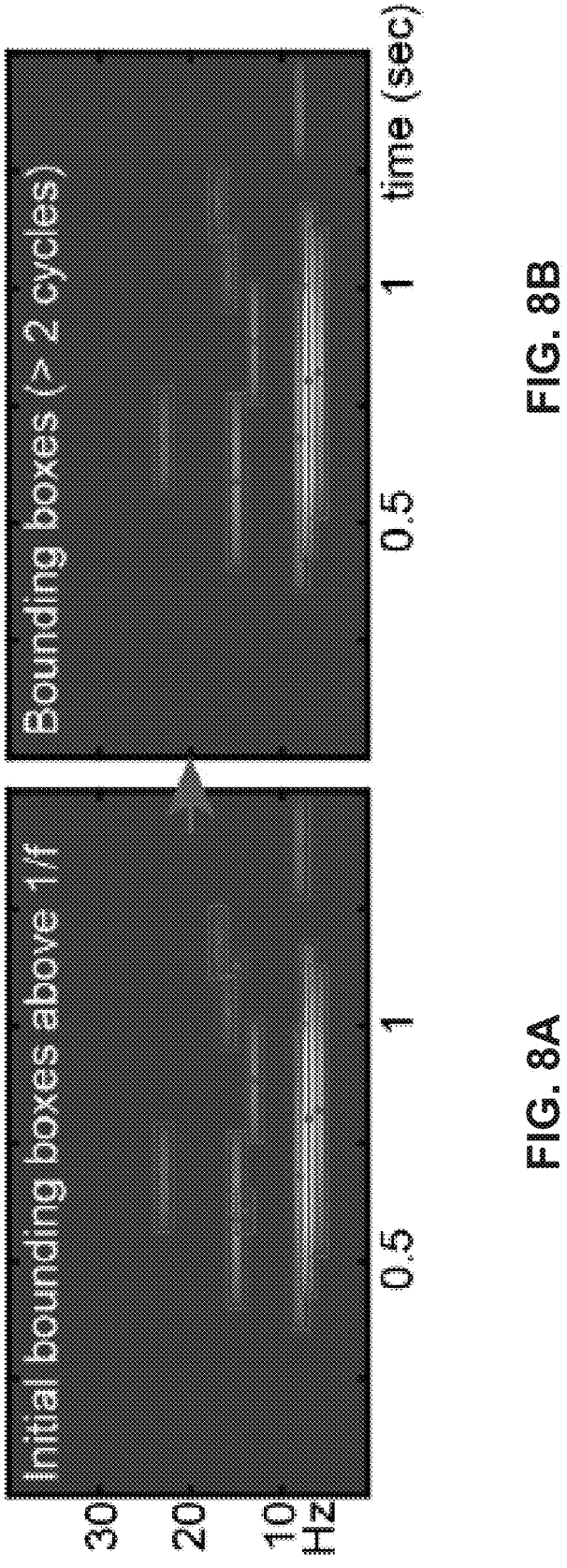
FIG. 8A is a graph showing an exemplary time vs. frequency map with identified oscillations (red bounding boxes).
FIG. 8B is a graph showing a time vs. frequency map modified from the map of FIG. 8A to remove oscillations with less than 2 cycles.

Referring again to FIG. 18, contiguous regions within the time-frequency space with spectral power above the 1/f threshold are enclosed by bounding boxes 2 (see also FIG. 8A) that capture the onset and offset times of the candidate oscillations. Each candidate oscillation within each bounding box is then evaluated and only those bounding boxes containing at least two oscillations are retained (see also FIG. 8B). Without being limited to any particular theory, oscillations of at least two cycles are thought to represent event-related potentials, evoked responses from a group of neurons by an external stimulus or event, and oscillation.

Figures 9A, 9B:
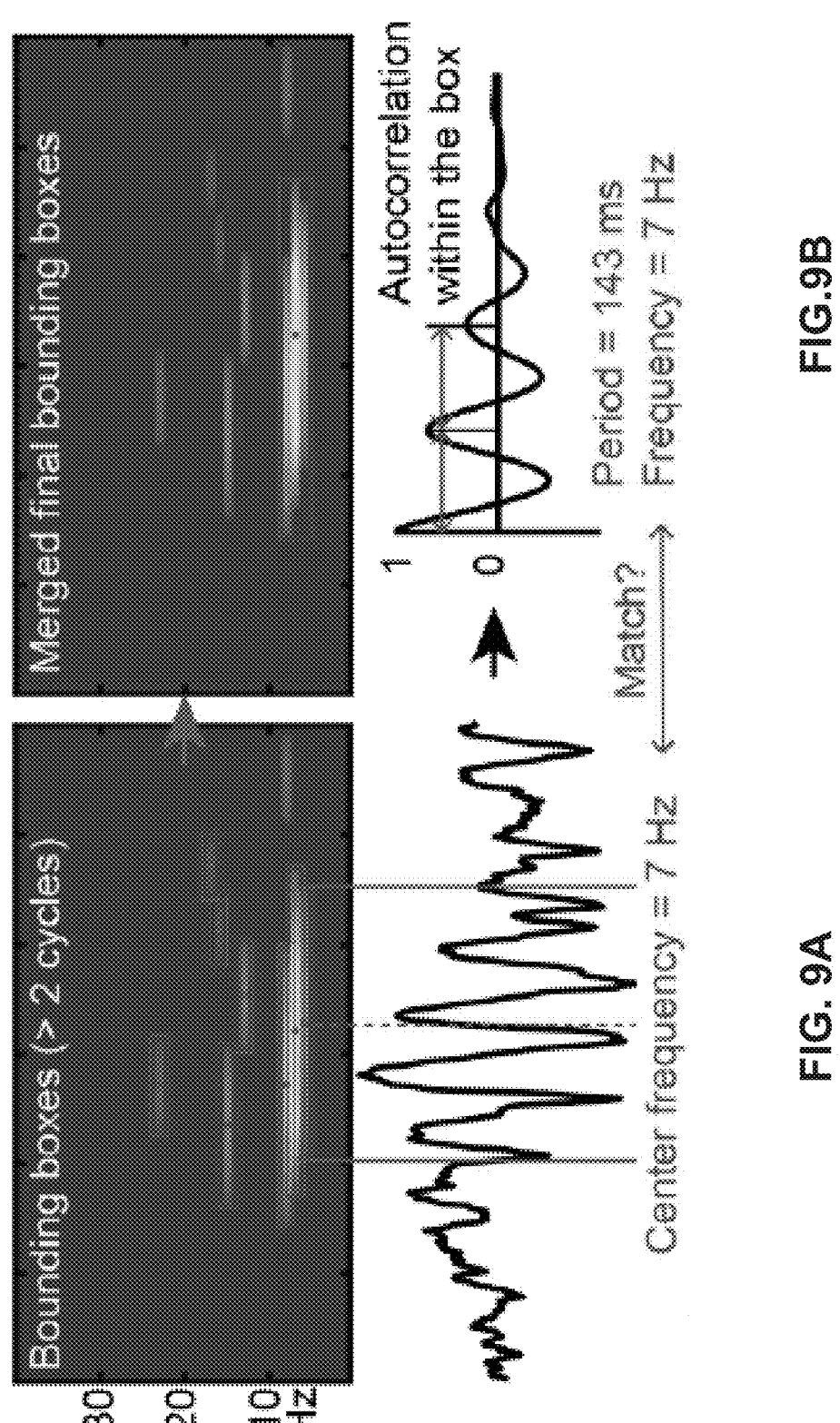
FIG. 9A is a graph showing a modified time vs. frequency map (see FIG. 8B) with identified oscillations (red bounding boxes) characterized by more than 2 cycles (top), along with its spectrum (bottom).
FIG. 9B is a graph showing a time vs. frequency map modified from FIG. 9A where only those oscillations that exhibit the same frequency as the corresponding autocorrelation are retained.
Figure 10:
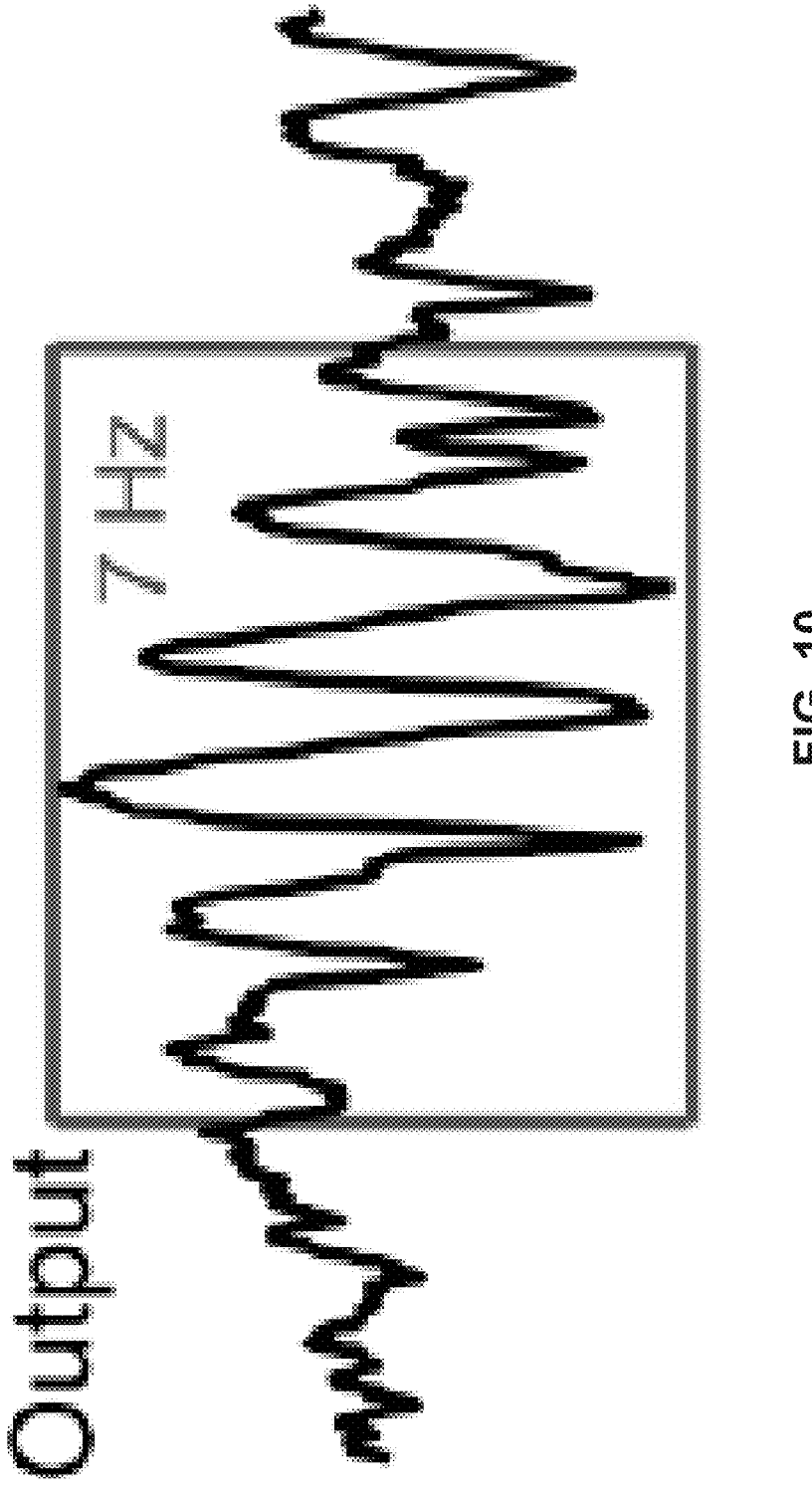
FIG. 10 is an exemplary graph summarizing the final output result obtained using the disclosed oscillation detection method, which illustrates the onset, offset, center frequency, frequency range, number of cycles, and degree of asymmetry for each detected oscillation.
Figure 11:
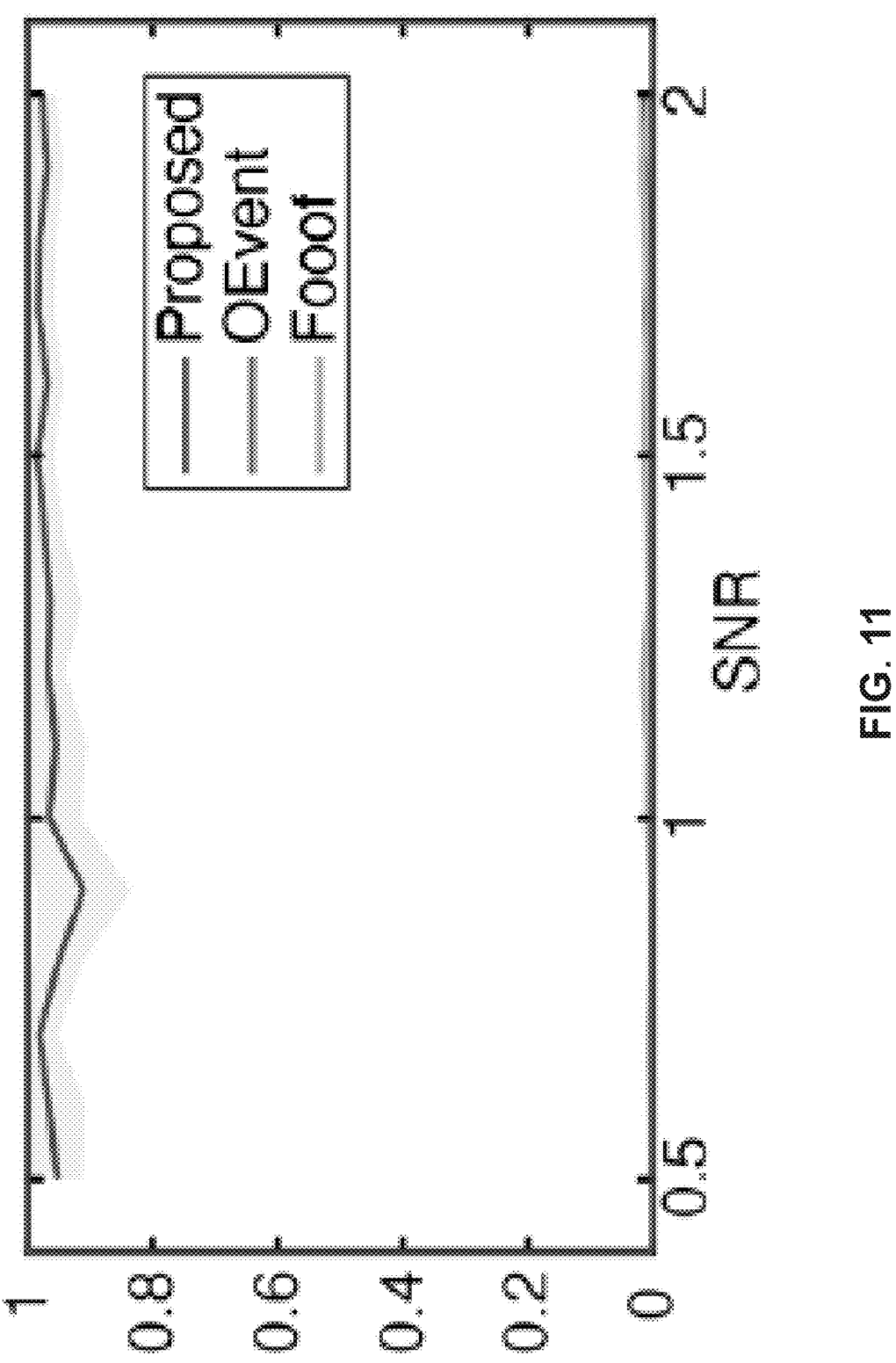
FIG. 11 is a graph summarizing a simulation of the specificity of the disclosed signal analysis method compared to existing oscillation detection methods (Fooof: fitting oscillations one over f; OEvent: oscillation event detection method).
Figure 12:
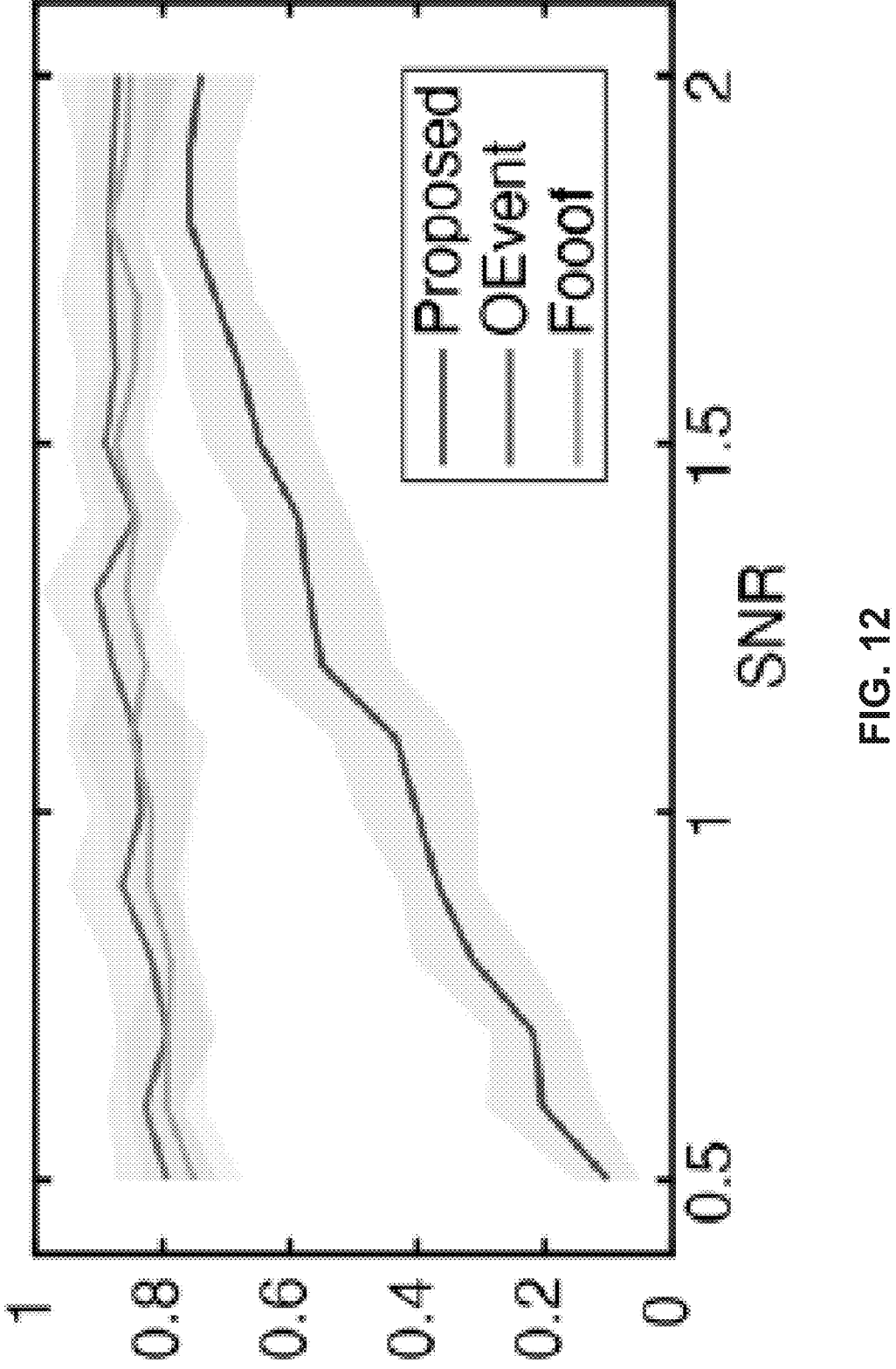
FIG. 12 is a graph summarizing a simulation of the sensitivity of the signal analysis method compared to the Fooof and OEvent methods.
Figure 13:
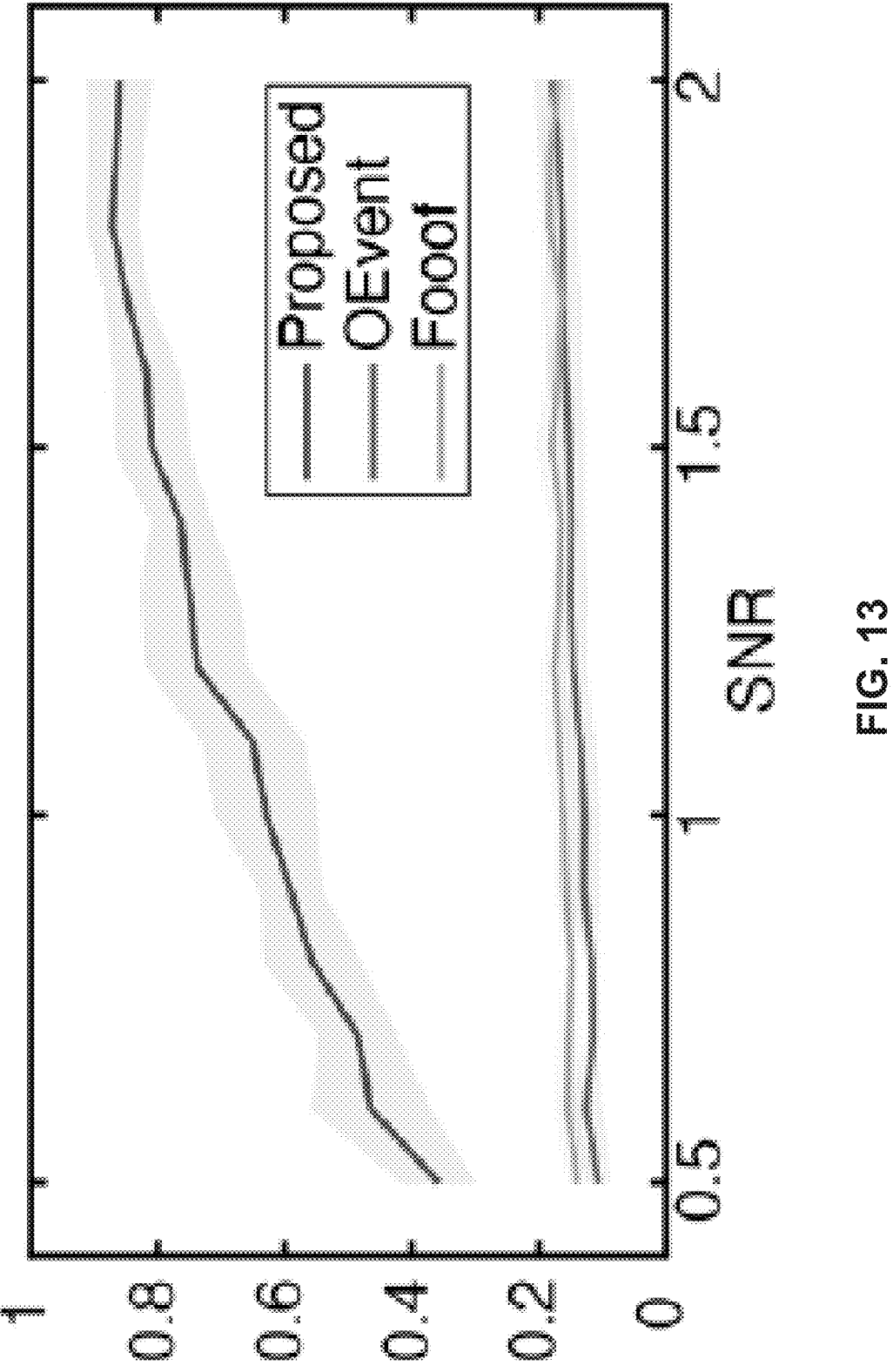
FIG. 13 is a graph summarizing a simulation of the accuracy of the signal analysis method compared to the Fooof and OEvent methods.
Figure 19:
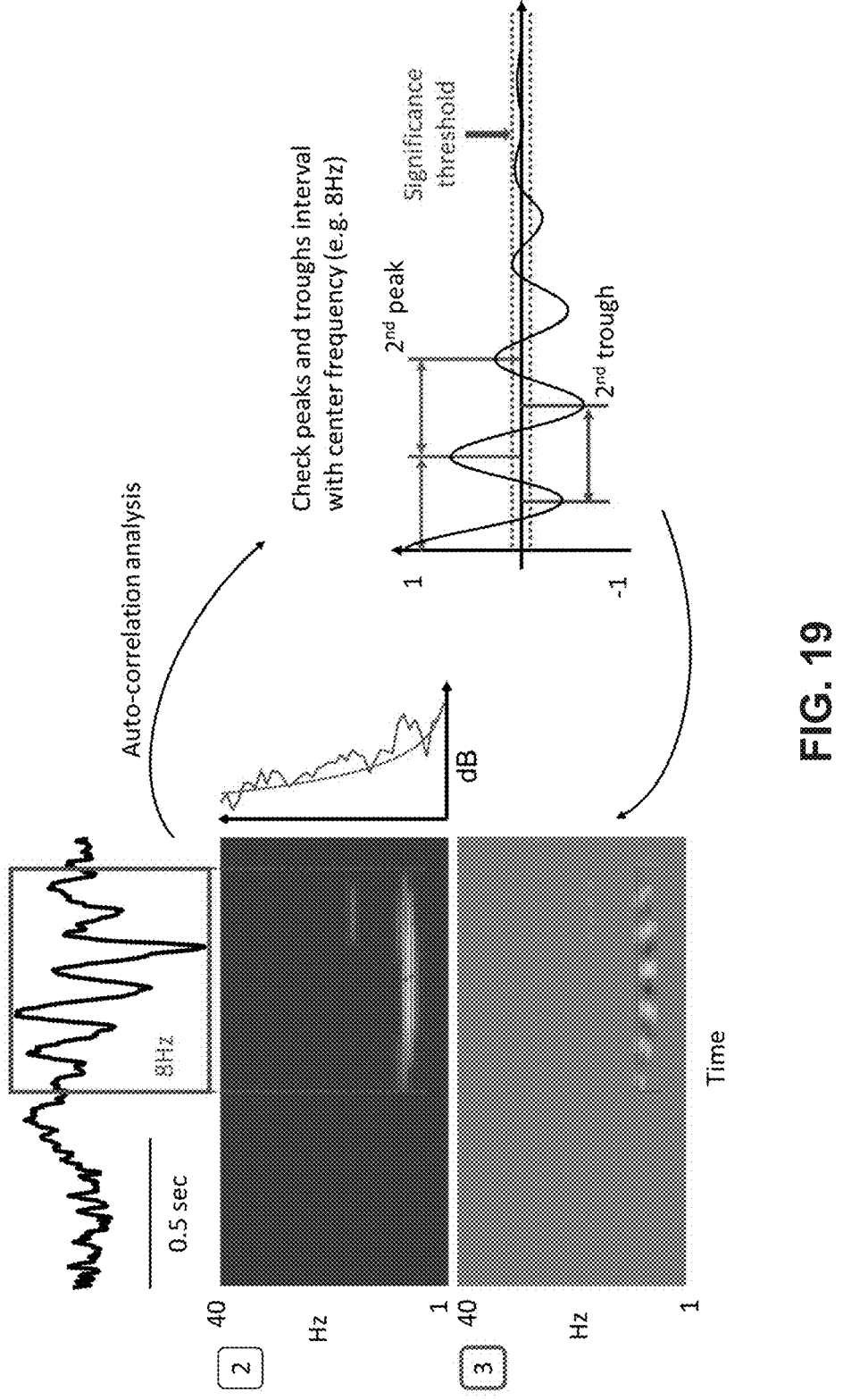
FIG. 19 is a schematic overview illustrating an autocorrelation analysis used by the disclosed oscillation detection method in one aspect.

As illustrated in FIG. 19, an autocorrelation is performed for data within the bounding boxes oscillations corresponding to at least 2 cycles that were identified as described above. As illustrated in FIG. 9A, the center frequency is identified within each selected bounding box, and only those oscillations that exhibit the same frequency as its autocorrelation are retained. While at least some existing oscillation detection methods consider all oscillations within the bounding boxes to be detected oscillations, the autocorrelation criterion of the method disclosed herein rejects spurious bounding boxes with harmonic frequency.

In various aspects, the disclosed oscillation method as described above yields the onset time, offset time, center frequency, frequency range, number of cycles, and degree of asymmetry for each detected oscillation.

Figure 20:
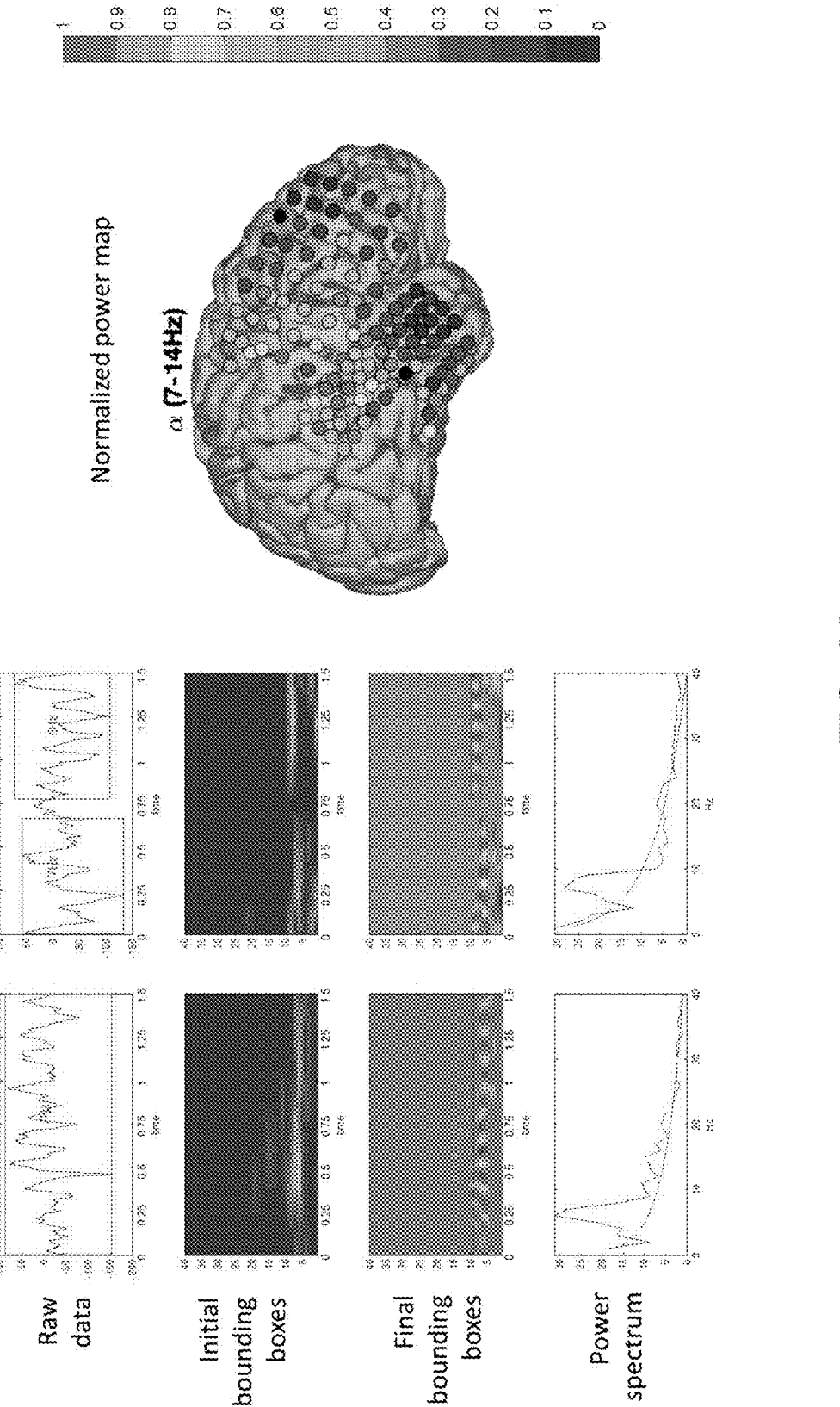
FIG. 20 contains a series of maps and graphs summarizing the detection and mapping of alpha oscillations detected using the disclosed oscillation detection method in one aspect.
Figure 21:
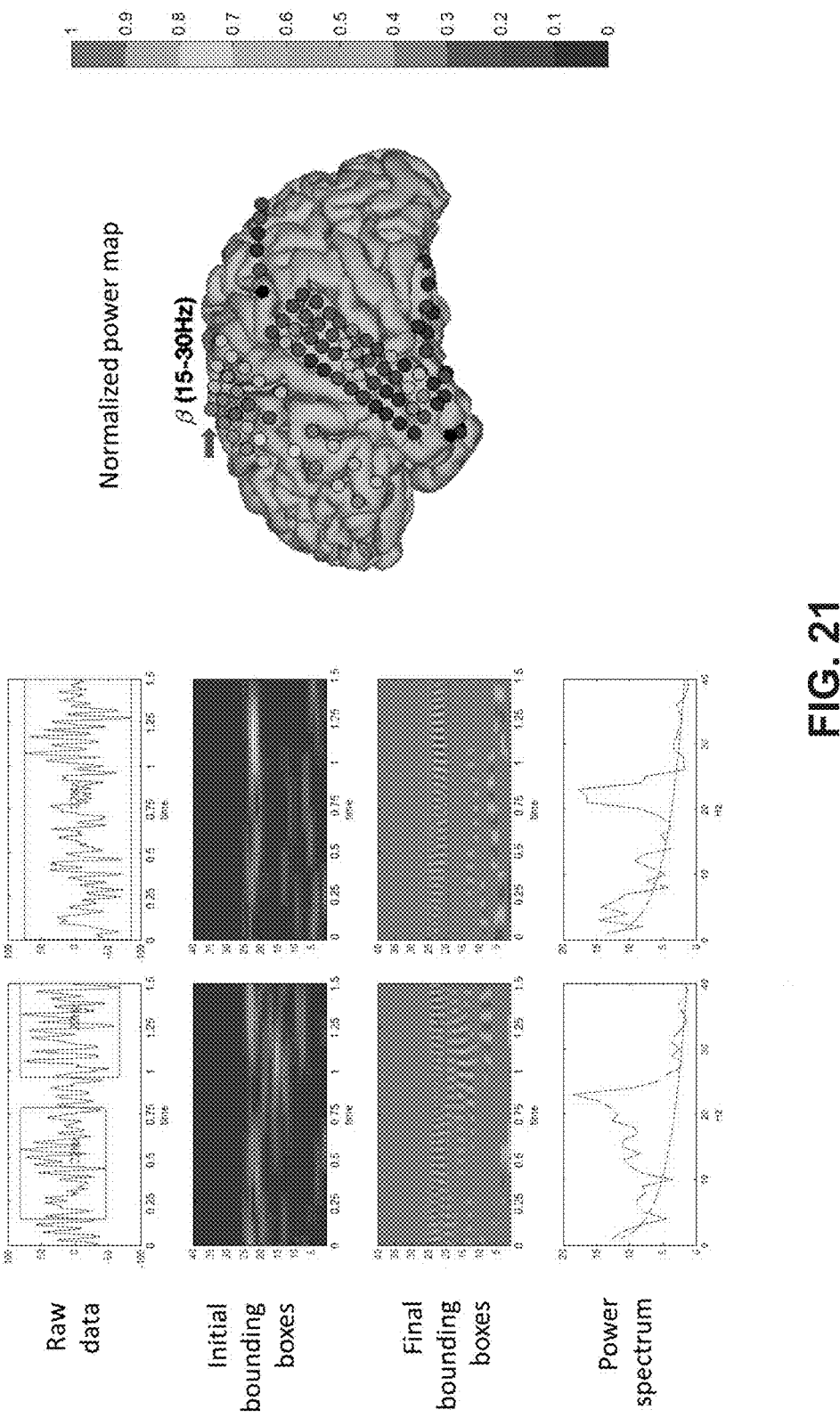
FIG. 21 contains a series of maps and graphs summarizing the detection and mapping of beta oscillations detected using the disclosed oscillation detection method in one aspect.
Figure 22:
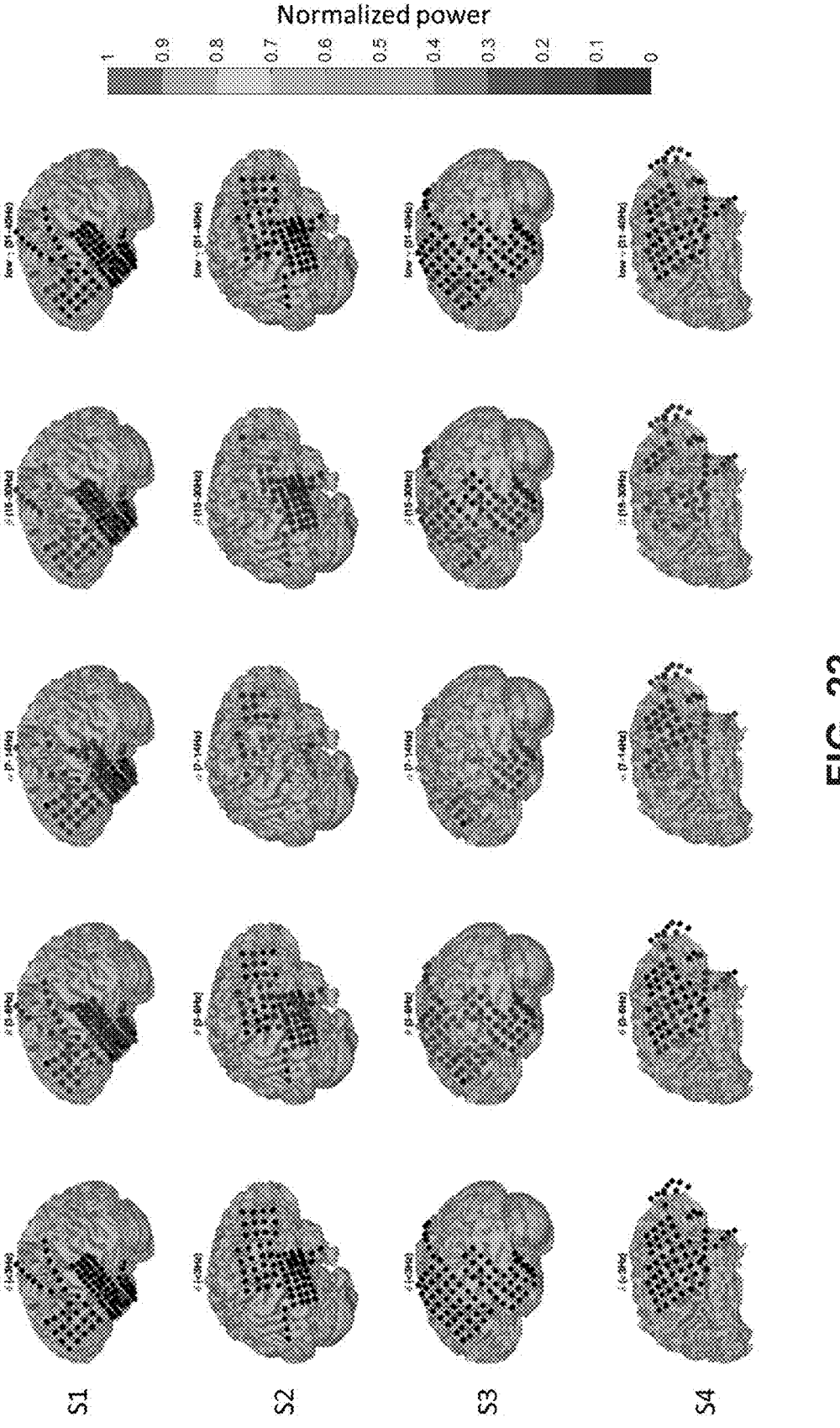
FIG. 22 contains a series of maps summarizing neural oscillations within various frequency ranges for a variety of subjects detected using the disclosed oscillation detection method in one aspect; each row contains maps from a single subject.
Figure 22:
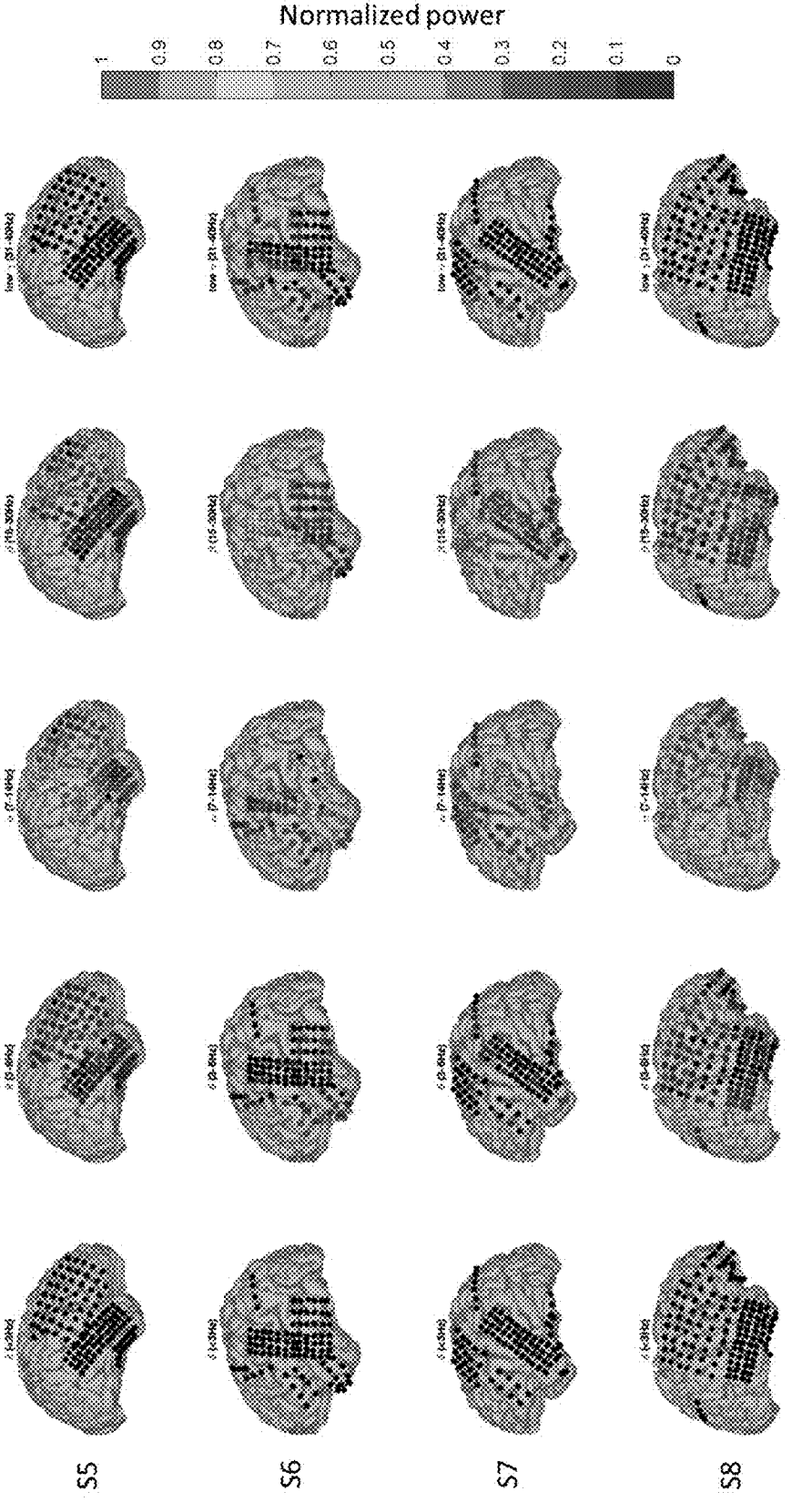
Figure 23:
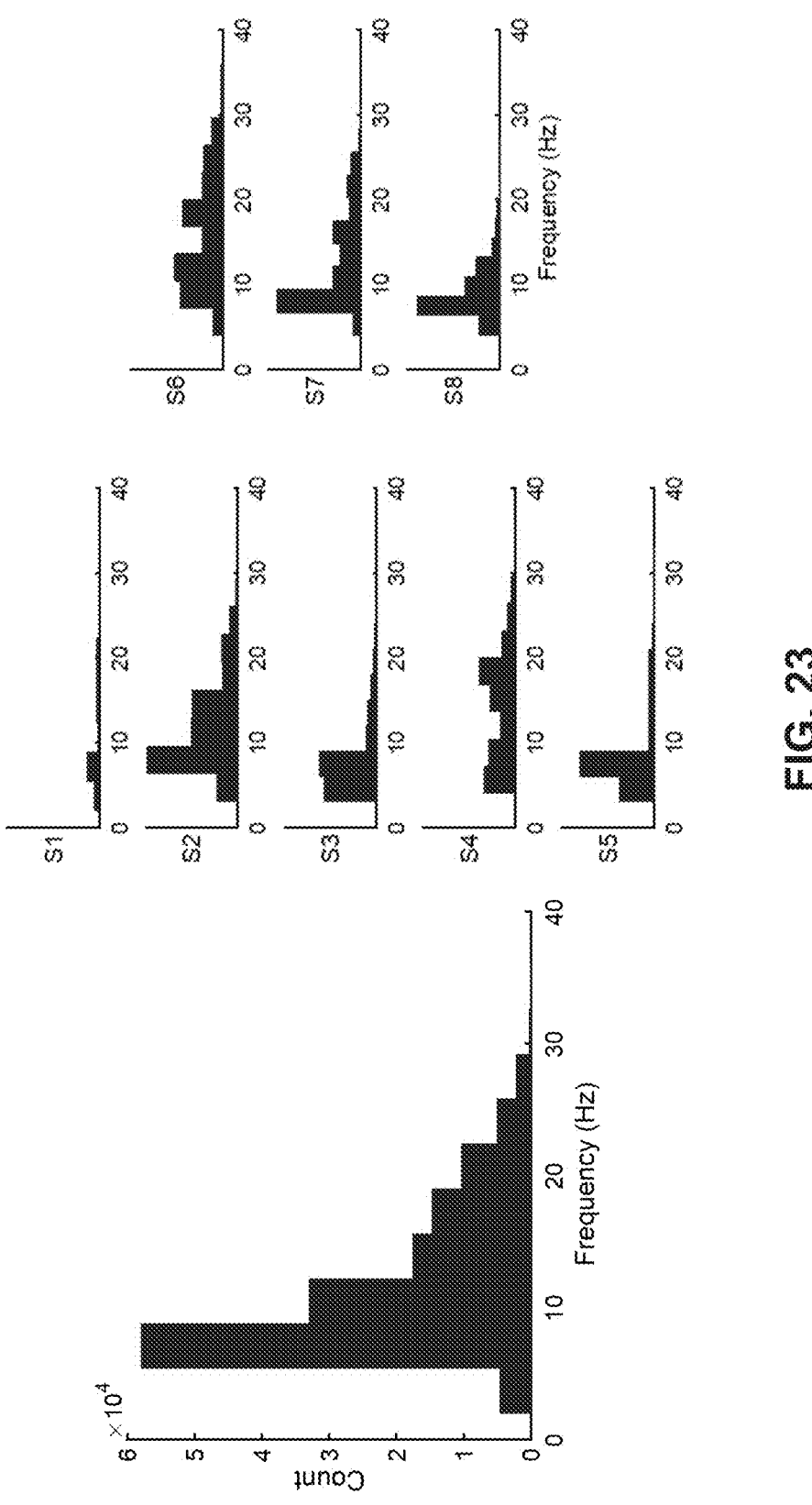
FIG. 23 contains histograms of peak frequencies detected using the disclosed oscillation detection method in one aspect, showing a combined population (left) and individual subjects (right).
Figure 24:
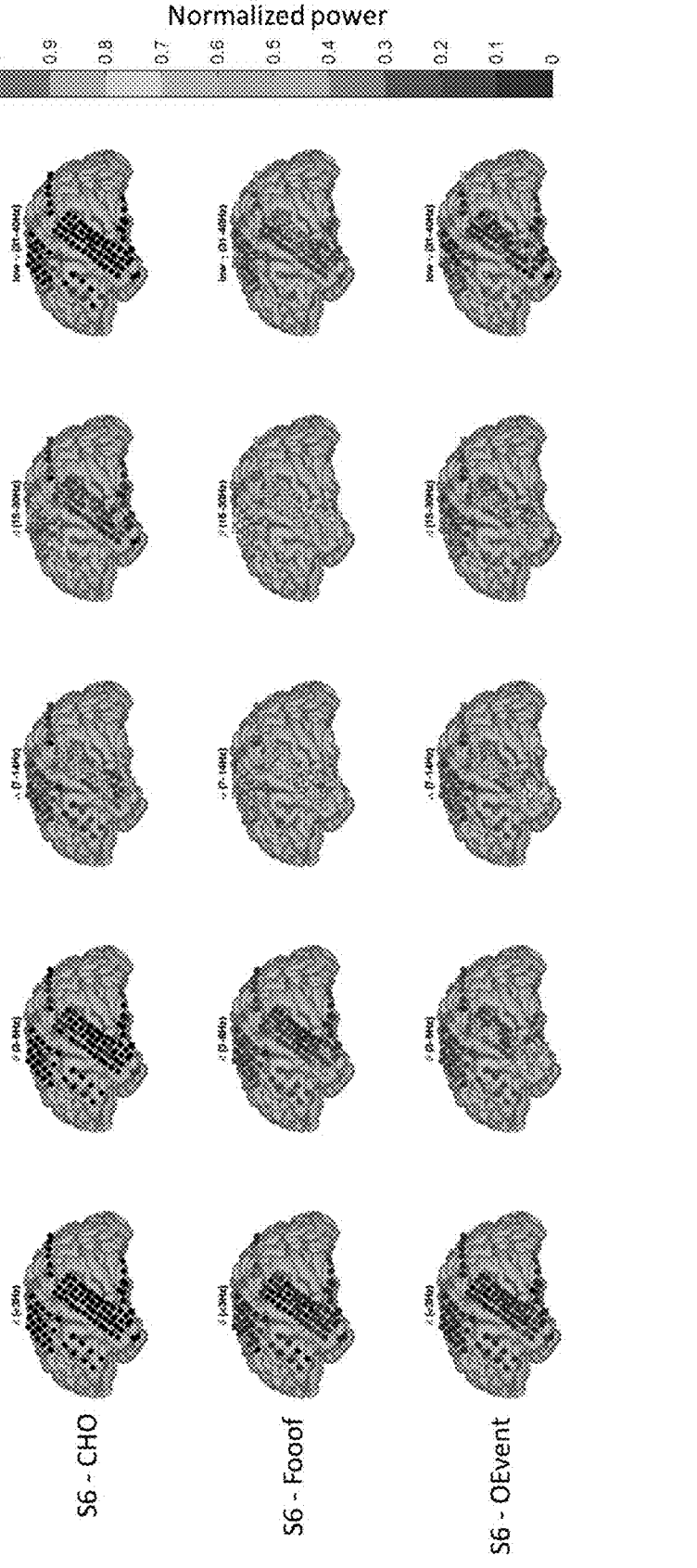
FIG. 24 contains a series of maps summarizing neural oscillations within various frequency ranges for one subject detected using the disclosed oscillation detection method (top row), Fooof (center row), and OEvent (bottom row).
Figure 25:
FIG. 25 is a summary of the variations in simulated signals used to produce simulated signals for validation of the disclosed oscillation detection method.
Figure 26:
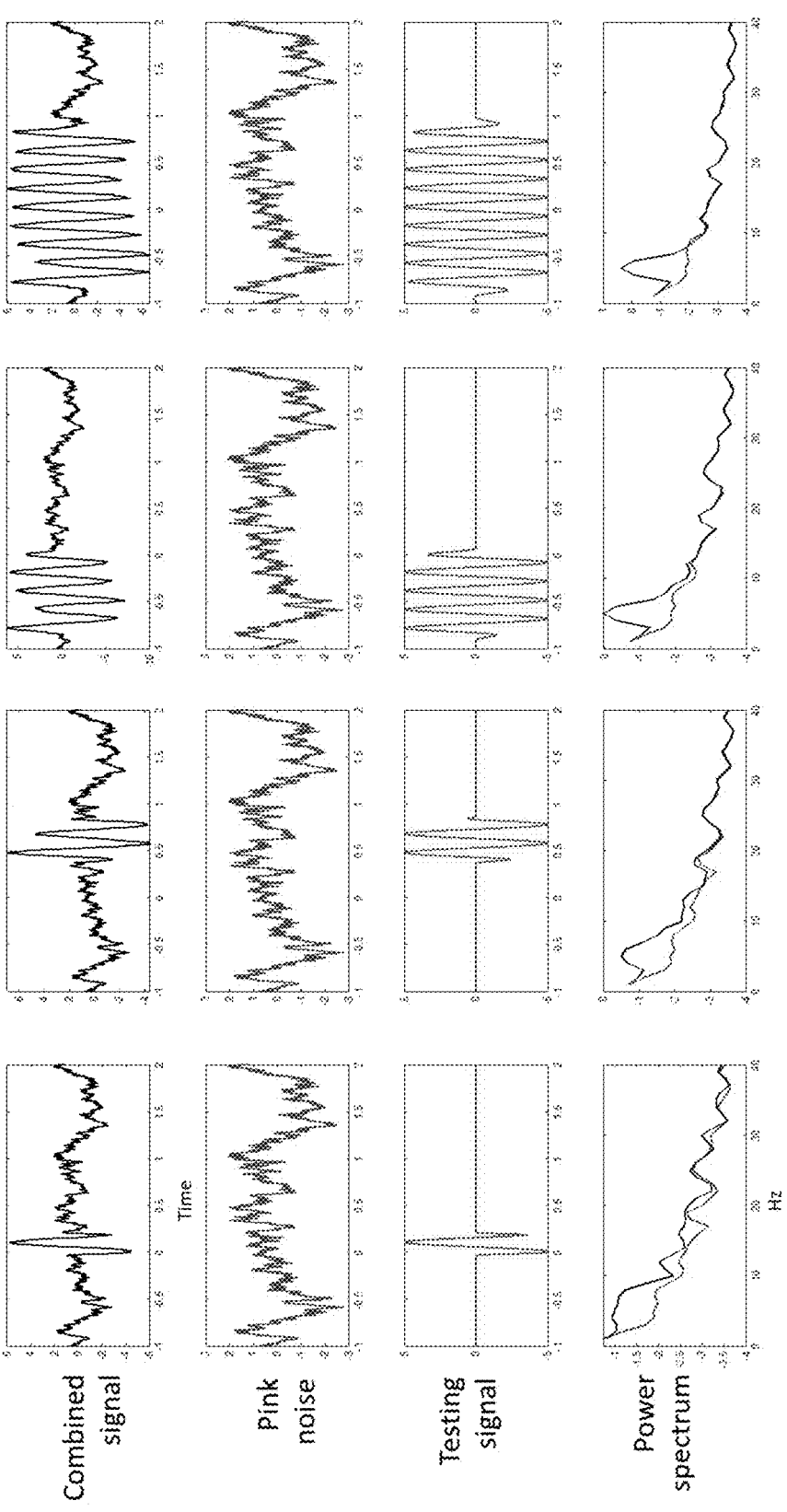
FIG. 26 contains a series of graphs summarizing simulated single sinusoid signals used to validate the disclosed oscillation detection method.
Figure 27:
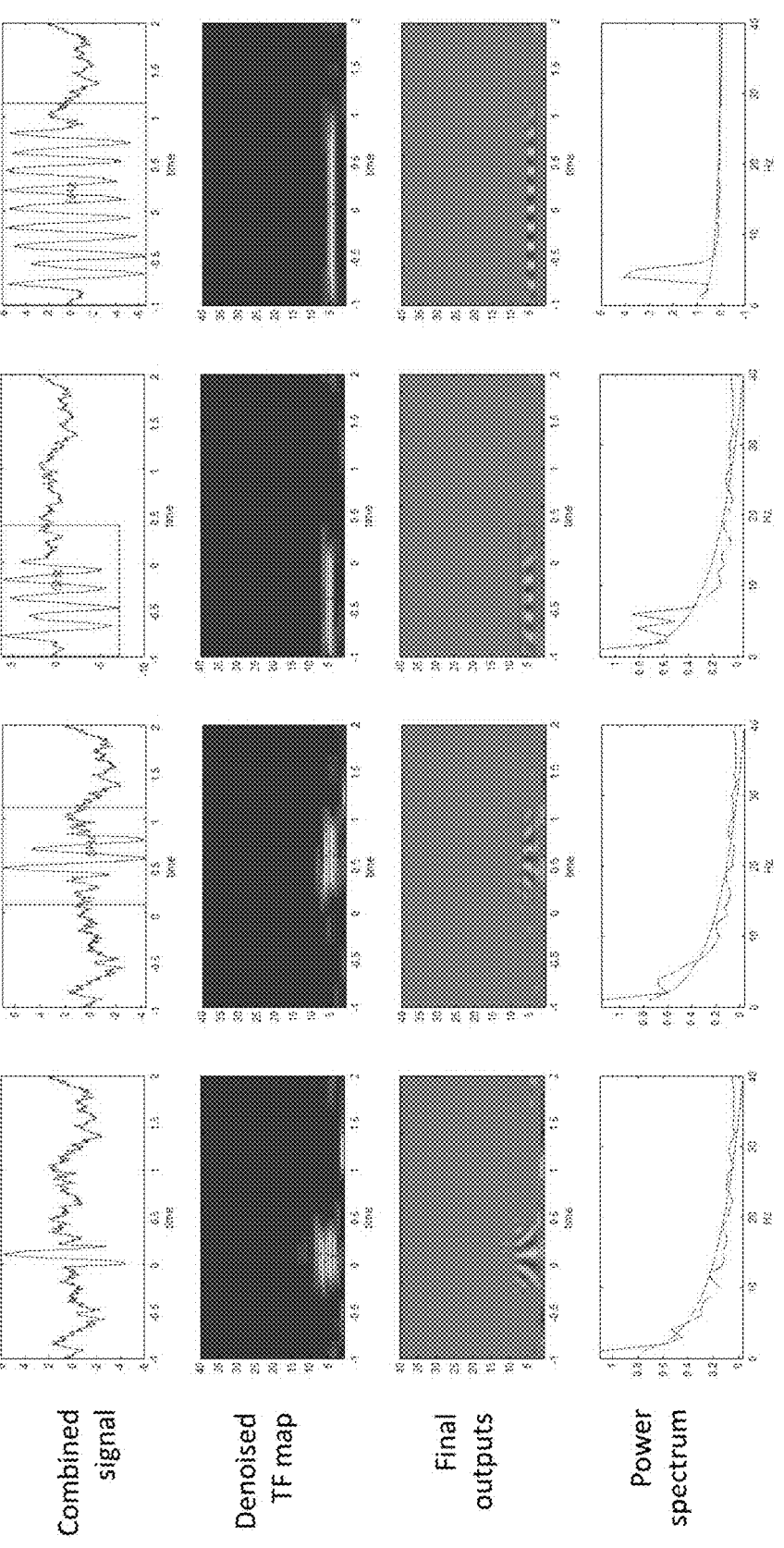
FIG. 27 contains a series of graphs summarizing the analysis of the simulated single sinusoid signals of FIG. 26 using the disclosed oscillation detection method.
Figure 28:
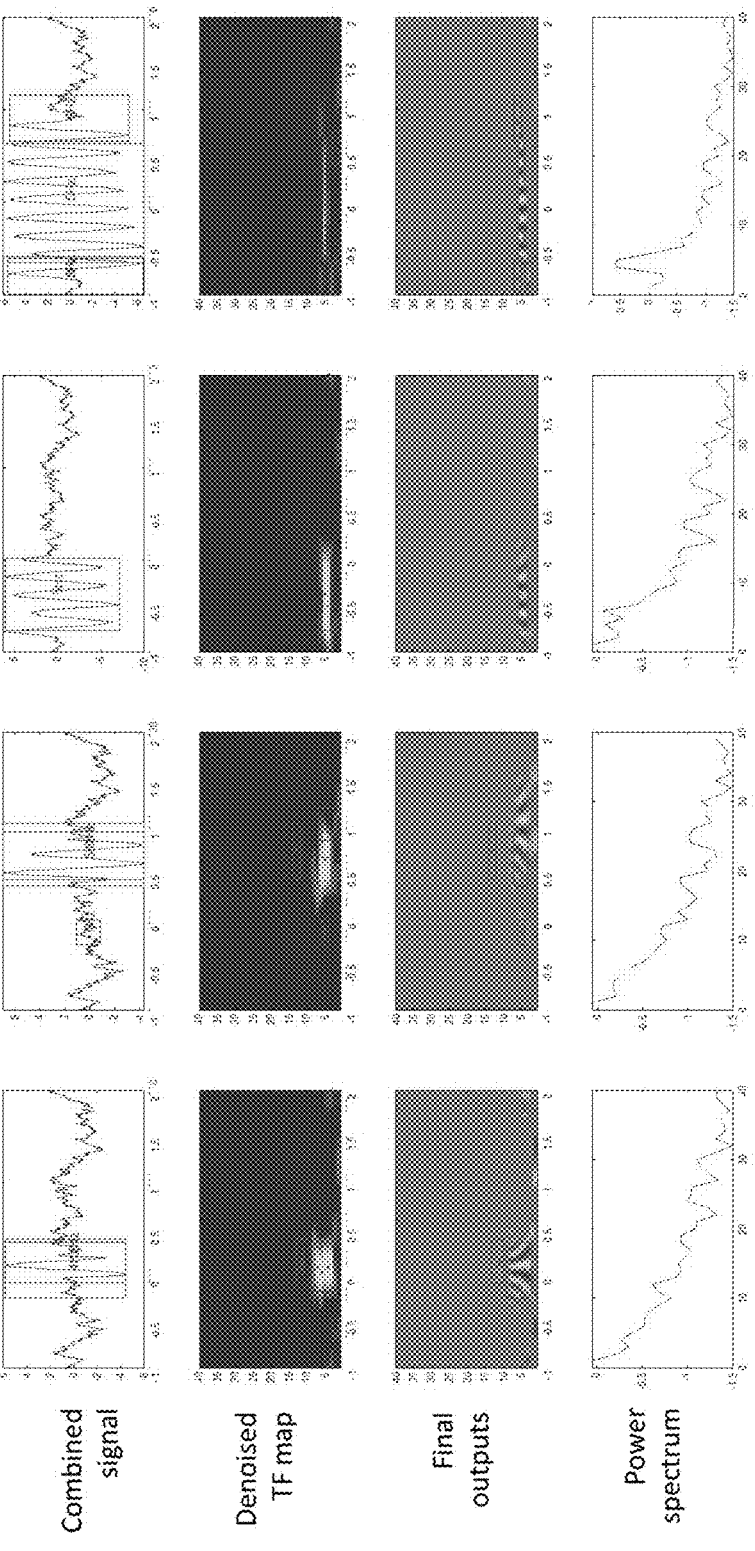
FIG. 28 contains a series of graphs summarizing the analysis of the simulated single sinusoid signals of FIG. 26 using an existing oscillation detection method, OEvent.

In various other aspects, the method disclosed herein may be used to identify multiple oscillations identified from EM electrode readings obtained from a plurality of positions over the brain of a subject. The oscillations may be grouped by frequency range and a normalized power map may be produced, as illustrated in FIG. 20 for alpha oscillations (7-14 Hz), and in FIG. 21 for beta oscillations (15-30 Hz). FIG. 22 contains corresponding maps for delta (<3 Hz), theta (3-6 Hz), alpha (7-14 Hz), beta (15-30 Hz), and low gamma (31-40 Hz) oscillations for a population of patients S1-S8. FIG. 23 contains histograms showing the distribution of detected oscillations by frequency for the individual patients of FIG. 22 (left) and for the combined patient population (left).

Figure 14:
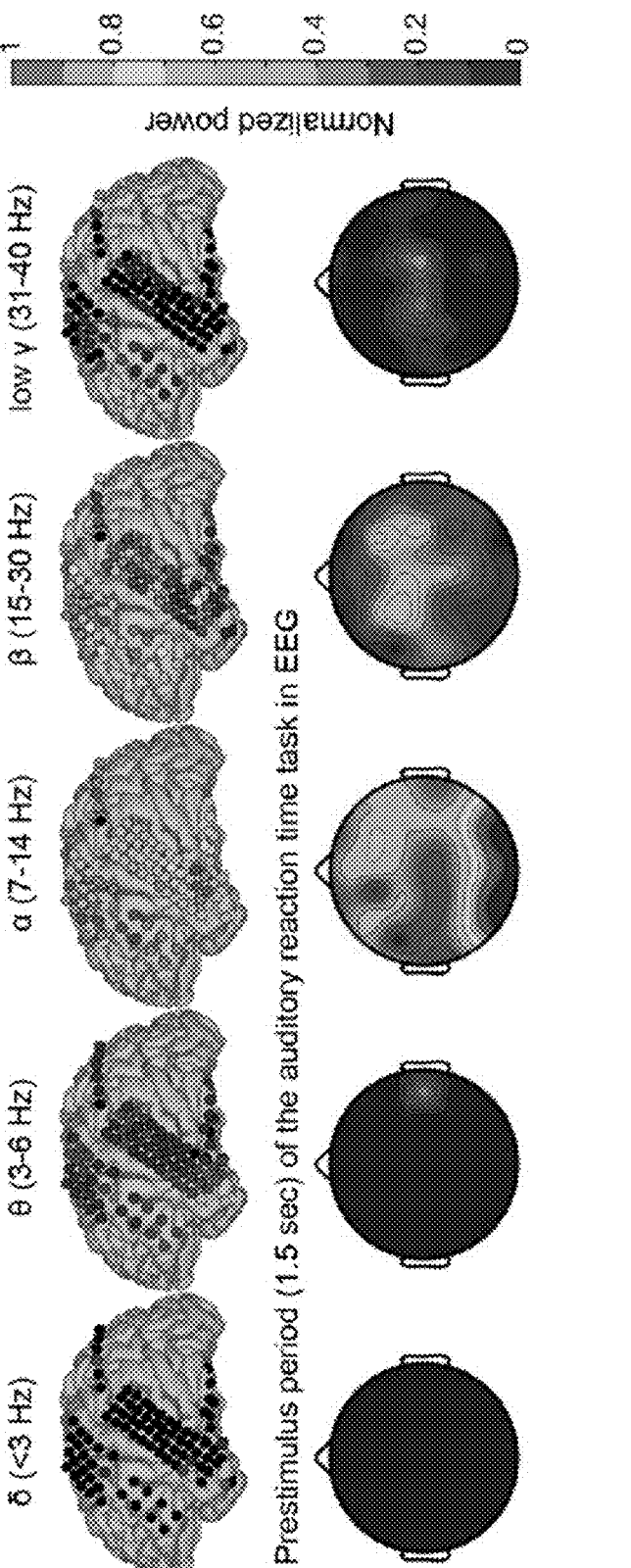
FIG. 14 contains a series of images summarizing the topographies of representative ECoG (top) and EEG subjects (bottom) for different frequency bands in ECoG and EEG. In ECoG, auditory alpha and pre-motor beta oscillations were detected, while occipital alpha and pre-motor beta oscillations were detected in EEG; task-relevant alpha and beta oscillations were detected in the pre-stimulus periods.
Figure 15:
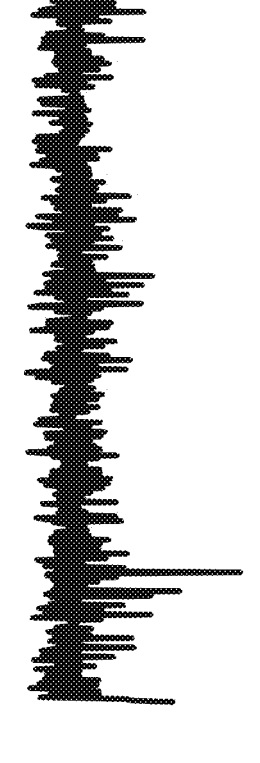
FIG. 15 is a schematic illustration comparing 1/f noise (left) and white noise (right) in the time (upper) and frequency (lower) domains.
Figure 15:
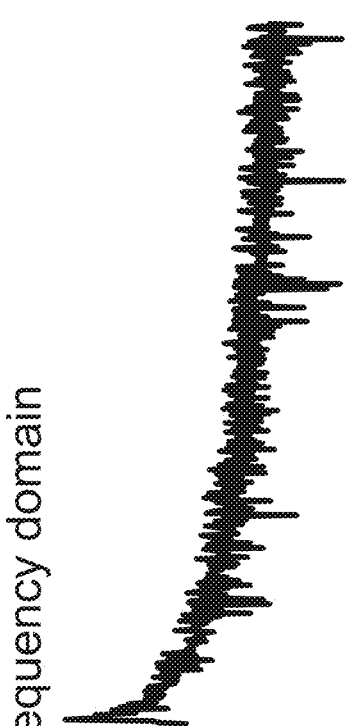
Figure 15:
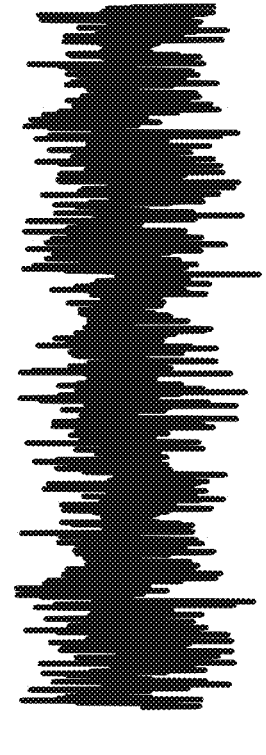
Figure 15:
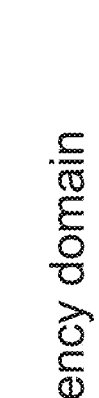

FIG. 14 is a comparison of an existing method and the disclosed method. We investigated topographies of oscillation detection for different frequency bands in electrocortigram (ECoG) and electroencephalogram (EEG). The topographic patterns were similar in the theta and alpha bands but different in the beta and gamma bands. This is because the existing methods still consider that harmonic frequencies are existing oscillations in the data, while the method disclosed herein filters out the spurious harmonic frequency components. In the resting period of an auditory reaction time task, beta oscillations were localized on the premotor area based on the disclosed method.

Figure 29:
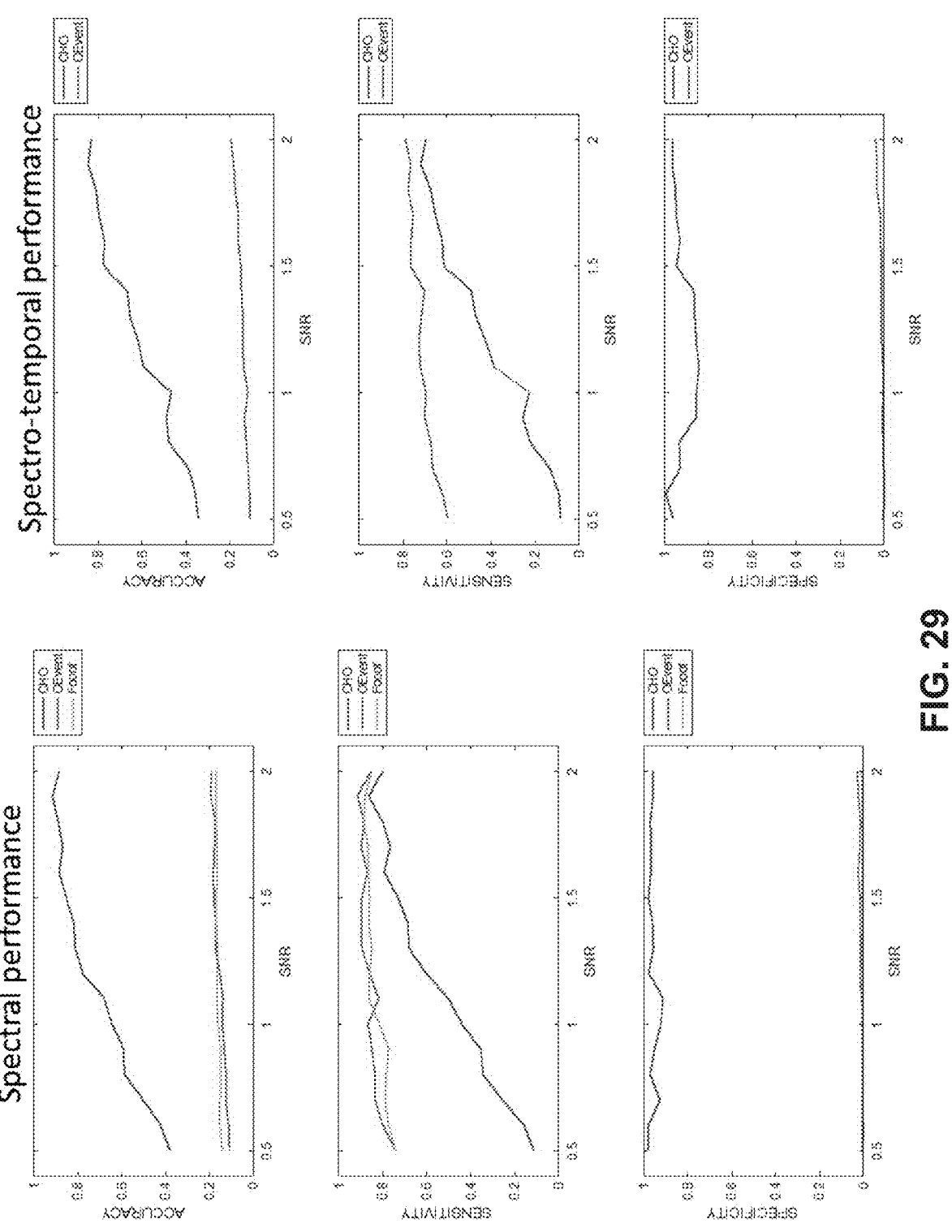
FIG. 29 contains a series of graphs comparing spectral and spectro-temporal performance on the simulated single sinusoid signals of FIG. 26 for the disclosed oscillation detection method and several existing oscillation detection methods.
Figure 30:
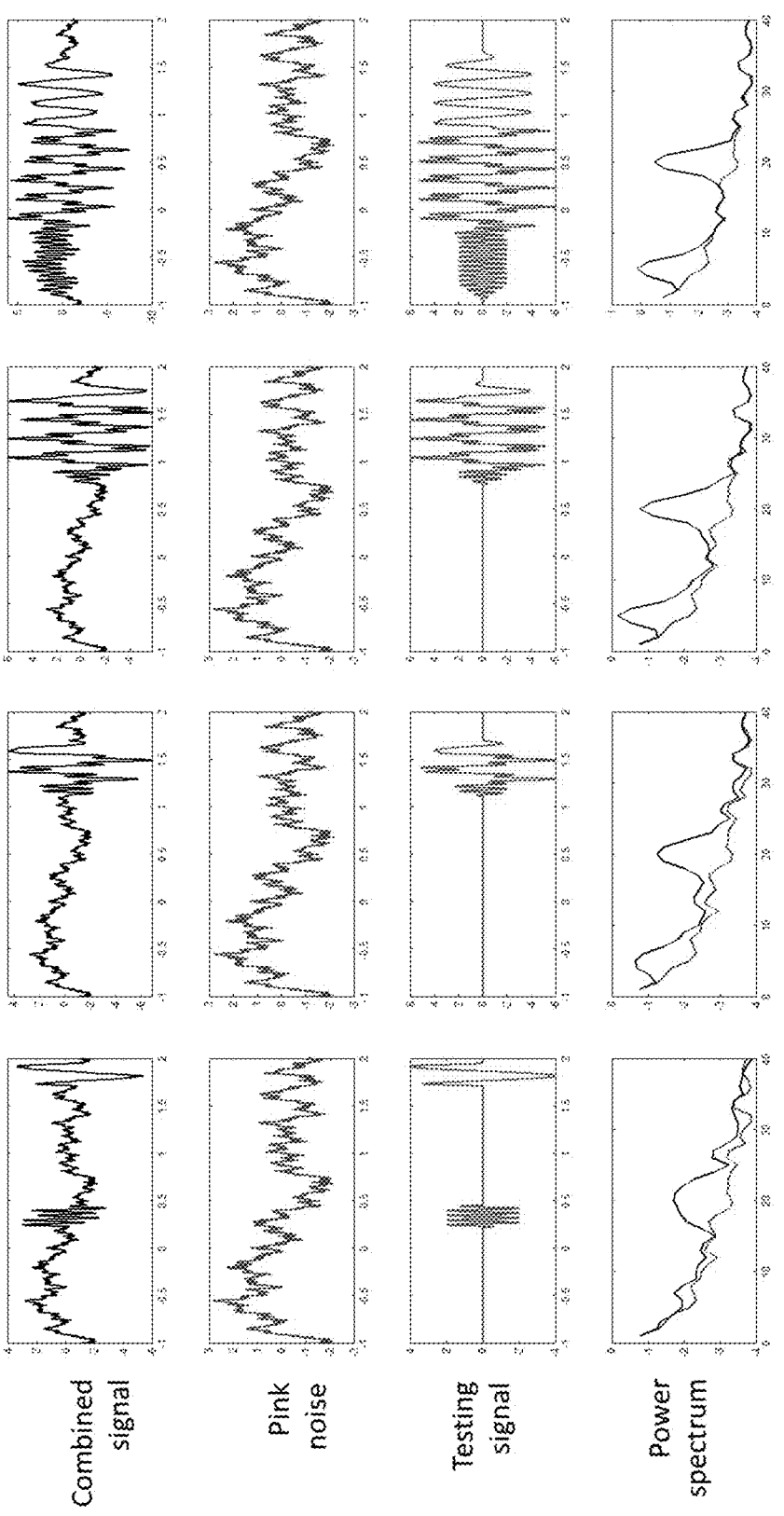
FIG. 30 contains a series of graphs summarizing simulated multiple sinusoid signals used to validate the disclosed oscillation detection method.
Figure 31:
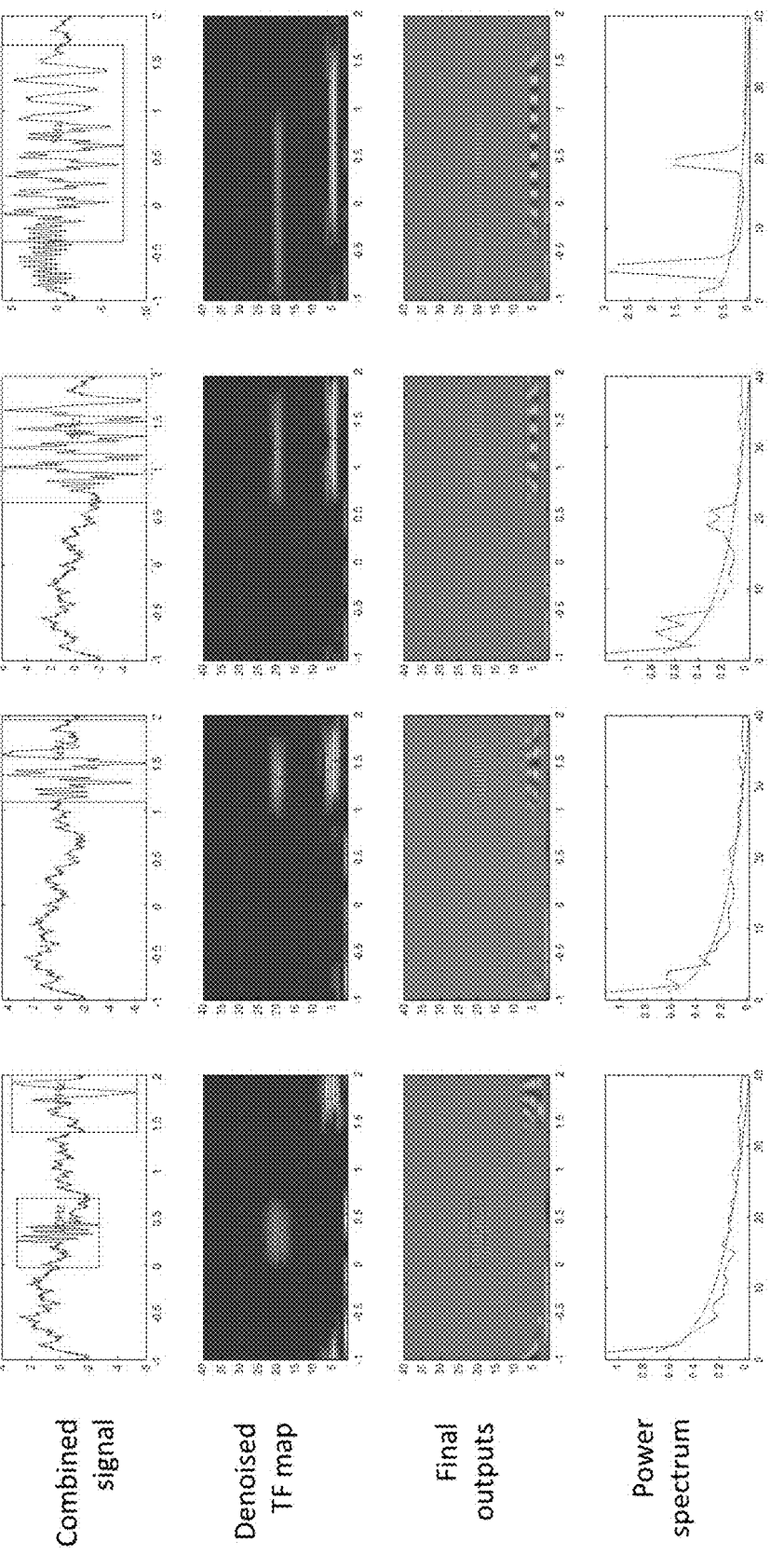
FIG. 31 contains a series of graphs summarizing the analysis of the simulated multiple sinusoid signals of FIG. 30 using the disclosed oscillation detection method.
Figure 32:
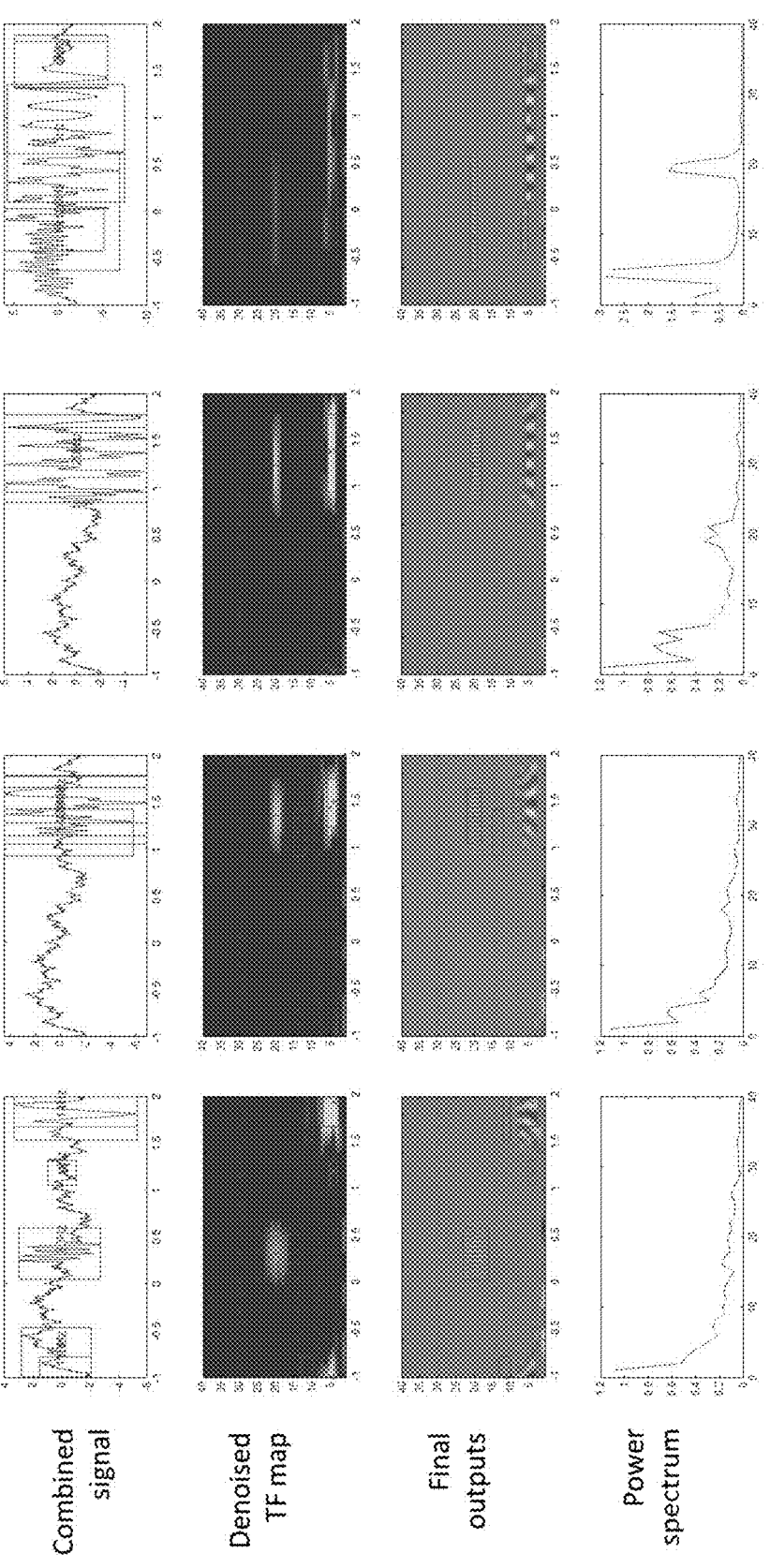
FIG. 32 contains a series of graphs summarizing the analysis of the simulated multiple sinusoid signals of FIG. 30 using an existing oscillation detection method, OEvent.
Figure 33:
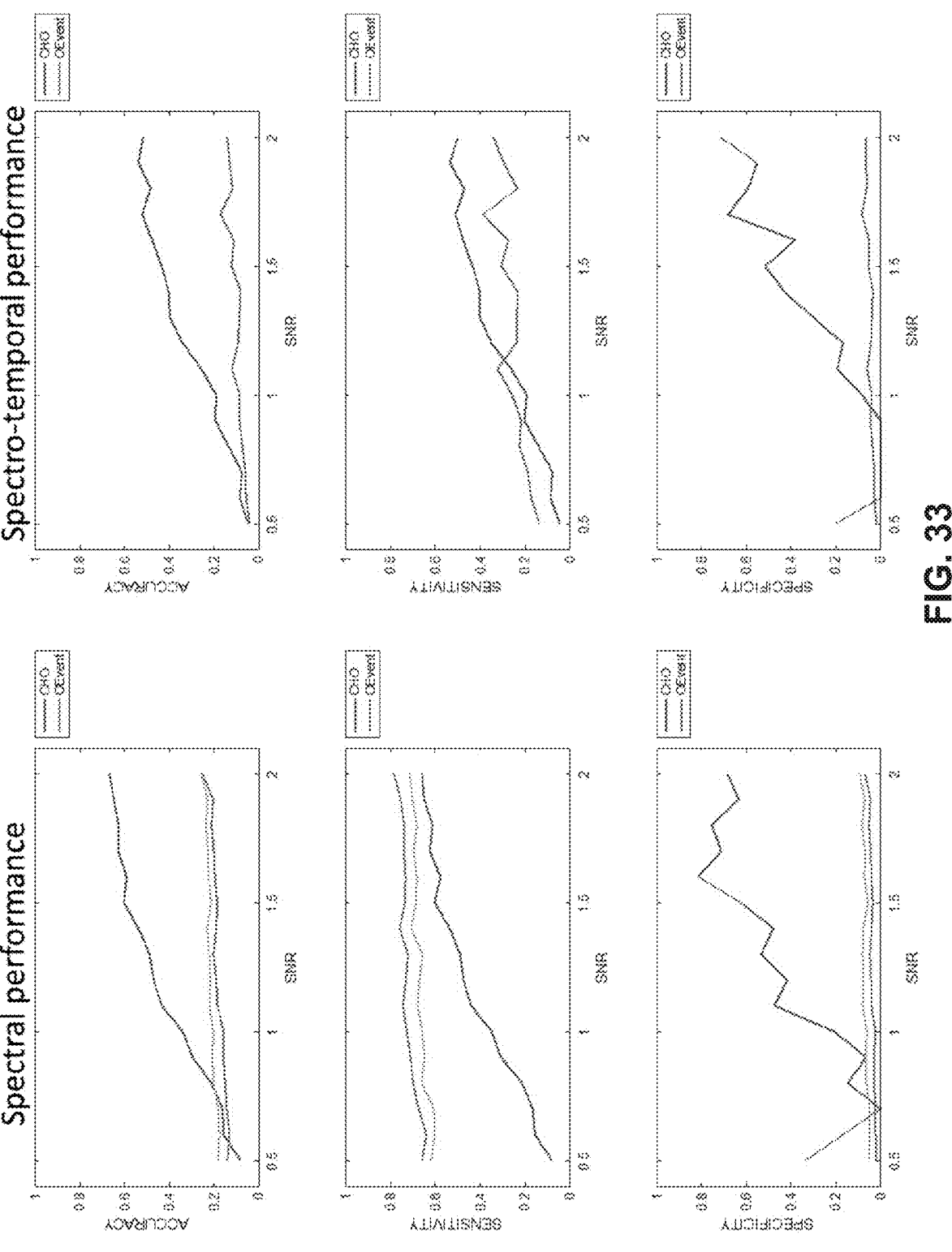
FIG. 33 contains a series of graphs comparing spectral and spectro-temporal performance on the simulated multiple sinusoid signals of FIG. 26 of the disclosed oscillation detection method to several existing oscillation detection methods.
Figure 34:
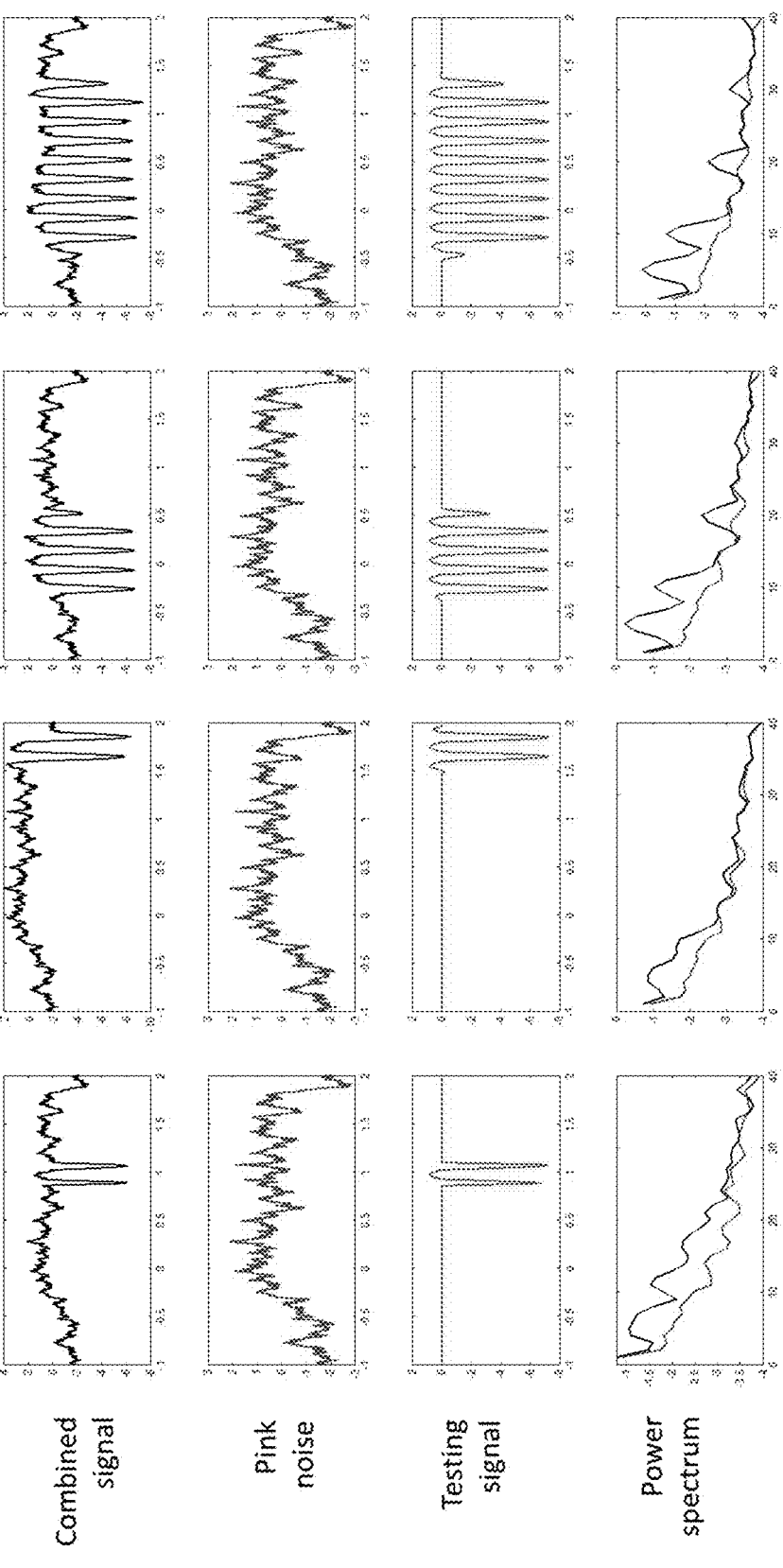
FIG. 34 contains a series of graphs summarizing simulated harmonic signals used to validate the disclosed oscillation detection method.
Figure 35:
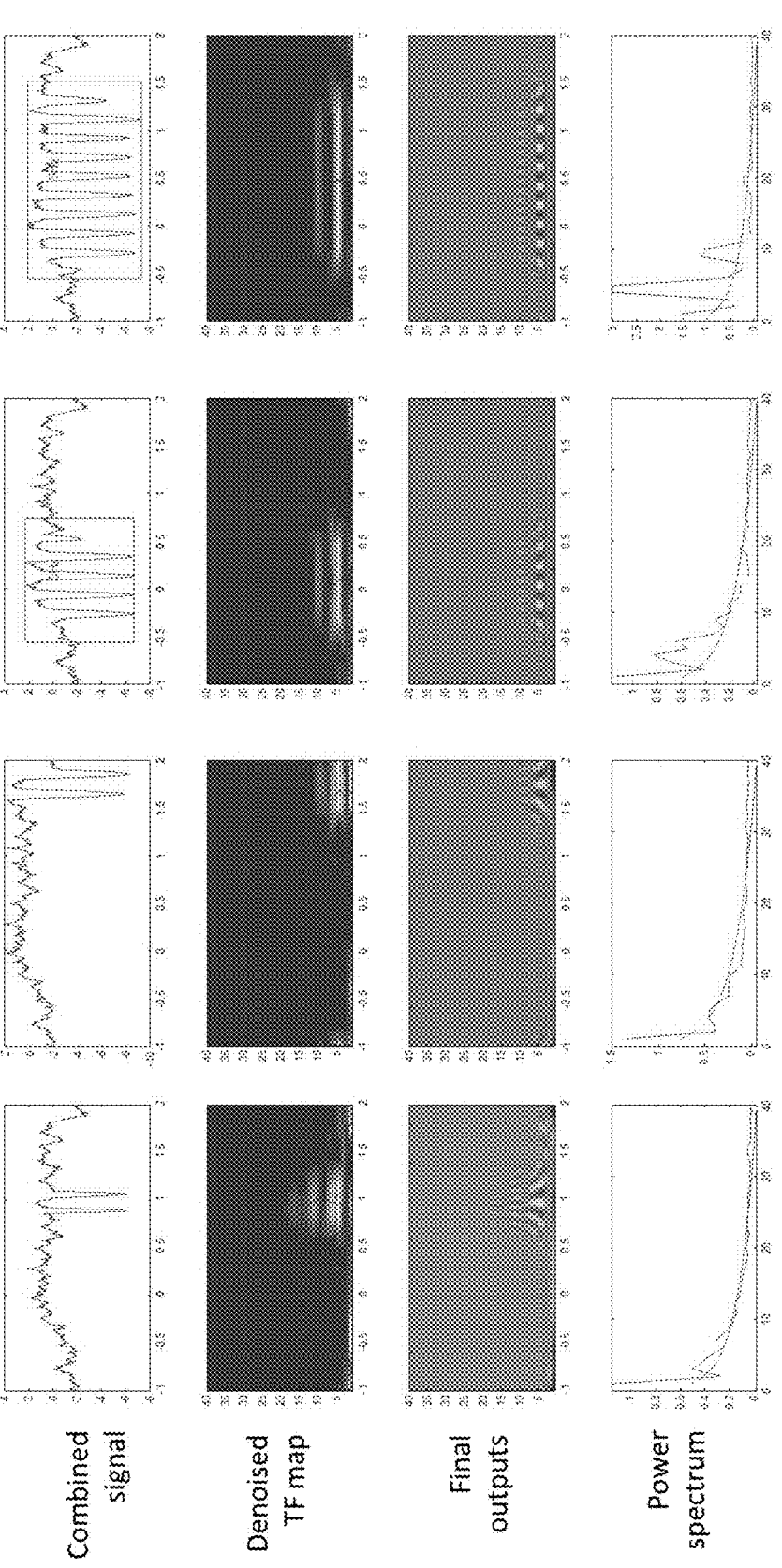
FIG. 35 contains a series of graphs summarizing the analysis of the simulated harmonic signals of FIG. 34 using the disclosed oscillation detection method.
Figure 36:
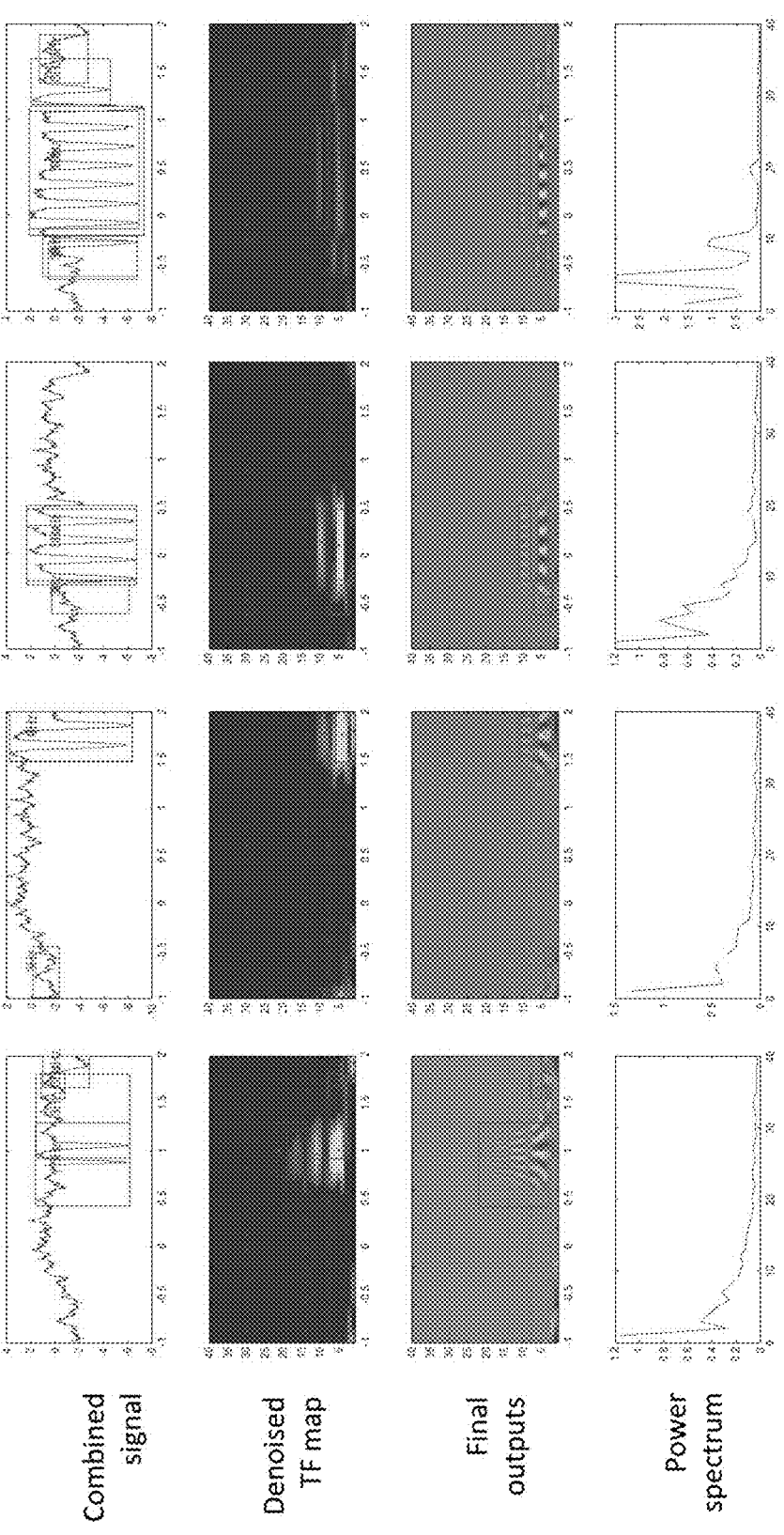
FIG. 36 contains a series of graphs summarizing the analysis of the simulated harmonic signals of FIG. 34 using an existing oscillation detection method, OEvent.
Figure 37:
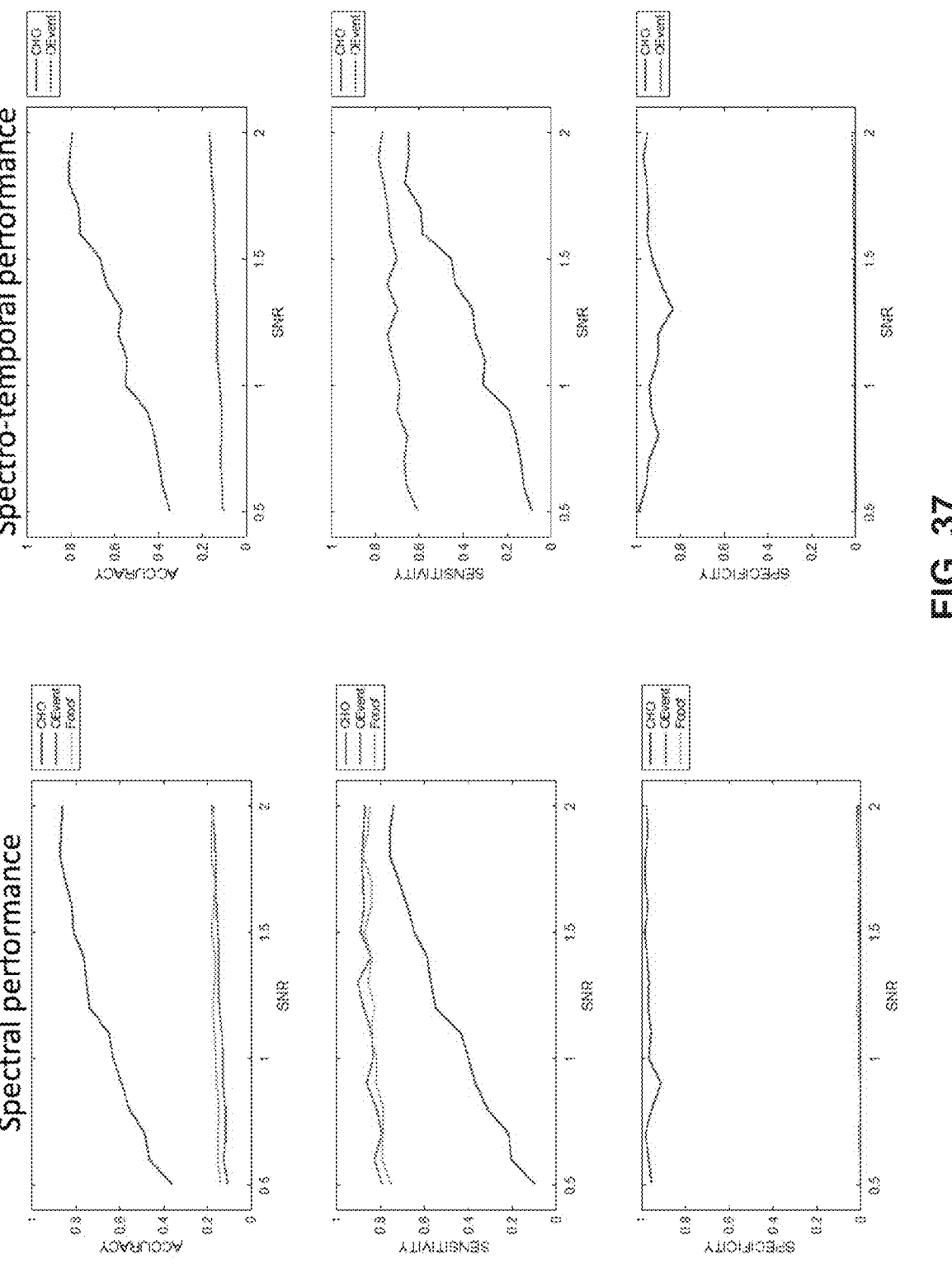
FIG. 37 contains a series of graphs comparing spectral and spectro-temporal performance on the simulated harmonic signals of FIG. 34 of the disclosed oscillation detection method to several existing oscillation detection methods.

The disclosed method and several existing methods including Fooof (fitting oscillations one over f, Donoghue et al. 2020) and OEvent (Oscillation event detection method, Neymotin et al. 2021 in preparation) were used to detect oscillations generated using simulation wave time histories (see FIGS. 25, 26, 27, and 28). As illustrated in FIGS. 14 and 29, the disclosed method outperformed Fooof and OEvent in regard to specificity and accuracy, but not in sensitivity. The disclosed method exhibited fewer false-positive detections and more true negative detections than other existing methods.

In various aspects, the disclosed method distinguishes 'true' neuronal oscillations from noise sources and is suitable for incorporation into a variety of systems and methods such as closed-loop systems (brain-computer interfaces and neurofeedback systems), and neural oscillation detection systems used to implement various neurological diagnostic and therapeutic methods.

In various aspects, at least a portion of the oscillation detection methods disclosed herein may be implemented using various computing systems and devices as described below.

FIG. 1 depicts a simplified block diagram of a computing device for implementing the oscillation detection methods described herein. As illustrated in FIG. 1, the computing device 300 may be configured to implement at least a portion of the tasks associated with the disclosed oscillation detection method, but not limited to: operating the EM activity monitoring system 310 to obtain neurophysiological signals and analyzing the neurophysiological signals to identify at least one oscillation as described herein. The computer system 300 may include a computing device 302. In one aspect, the computing device 302 is part of a server system 304, which also includes a database server 306. The computing device 302 is in communication with a database 308 through the database server 306. The computing device 302 is communicably coupled to the EM activity monitoring system 310 and a user-computing device 330 through a network 350. The network 350 may be any network that allows local area or wide area communication between the devices. For example, the network 350 may allow communicative coupling to the Internet through at least one of many interfaces including, but not limited to, at least one of a network, such as the Internet, a local area network (LAN), a wide area network (WAN), an integrated services digital network (ISDN), a dial-up-connection, a digital subscriber line (DSL), a cellular phone connection, and a cable modem. The user-computing device 330 may be any device capable of accessing the Internet including, but not limited to, a desktop computer, a laptop computer, a personal digital assistant (PDA), a cellular phone, a smartphone, a tablet, a phablet, wearable electronics, smartwatch, or other web-based connectable equipment or mobile devices.

Figure 2:
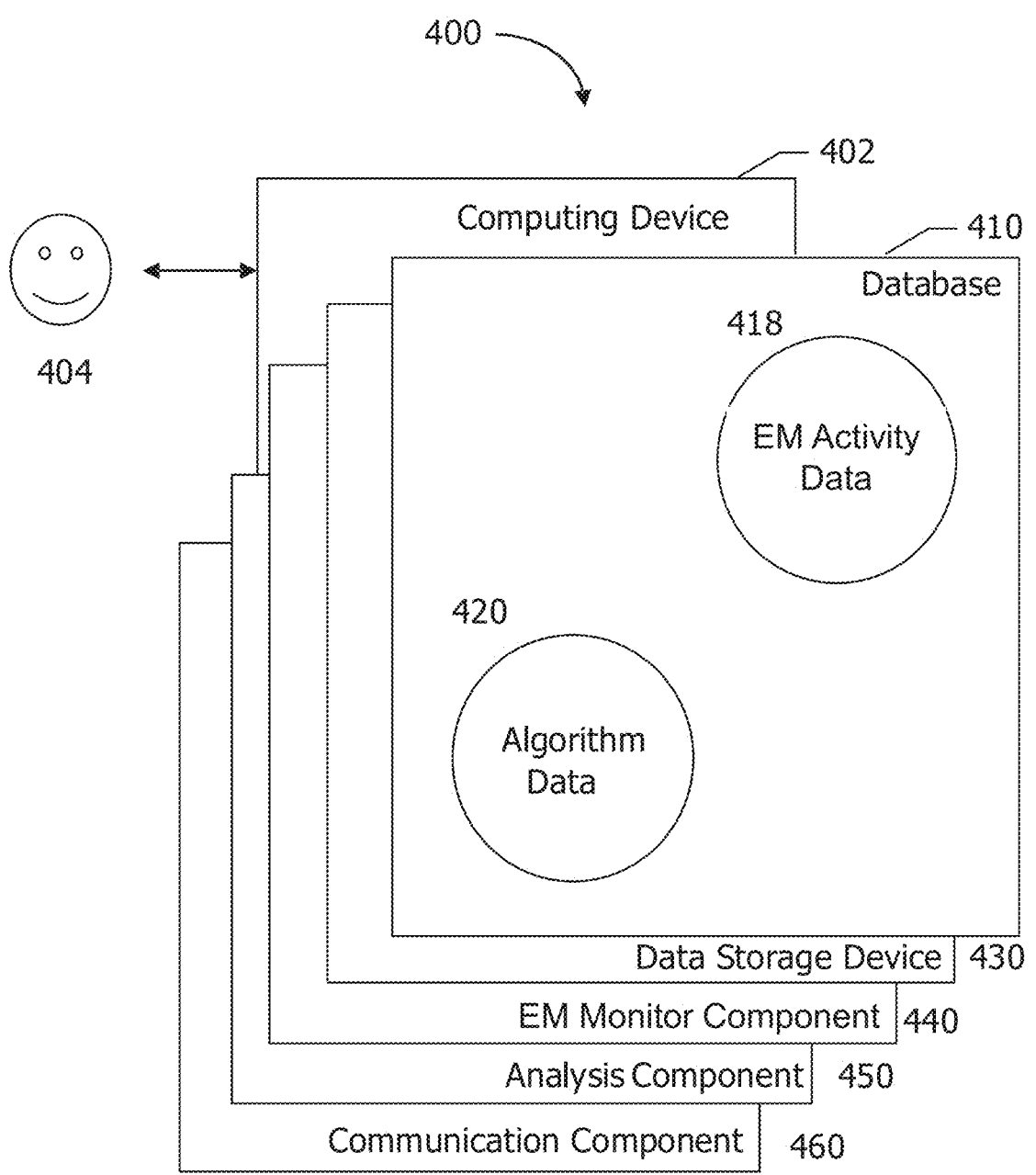
FIG. 2 is a block diagram schematically illustrating a computing device in accordance with one aspect of the disclosure.

In other aspects, the computing device 302 is configured to perform a plurality of tasks associated with the disclosed oscillation detection methods described herein. FIG. 2 depicts a component configuration 400 of computing device 402, which includes database 410 along with other related computing components. In some aspects, computing device 402 is similar to computing device 302 (shown in FIG. 1). A user 404 may access components of computing device 402. In some aspects, database 410 is similar to database 308 (shown in FIG. 1).

In one aspect, database 410 includes EM activity data 418 and algorithm data 420. Non-limiting examples of EM activity data 418 include any data quantifying neurophysiological signals or neural signals indicative of electromagnetic (EM) activity of the brain. Non-limiting examples of suitable algorithm data 420 include any values of parameters defining the analysis of the neurophysiological signals or neural signals according to the oscillation detection methods disclosed herein. Other non-limiting examples of suitable algorithm data 420 include any parameters defining the formatting of reports of results.

Computing device 402 also includes a number of components that perform specific tasks. In the exemplary aspect, computing device 402 includes a data storage device 430, an EM monitor component 440, analysis component 450, and communication component 460. Data storage device 430 is configured to store data received or generated by computing device 402, such as any of the data stored in database 410 or any outputs of processes implemented by any component of computing device 402. EM monitor component 440 is configured to operate or produce signals configured to operate, an EM activity monitoring system to neurophysiological signals or neural signals indicative of electromagnetic (EM) activity of the brain. The analysis component 450 is configured to analyze the EM activity data 418 to identify at least one oscillation according to the methods disclosed herein.

Communication component 460 is configured to enable communications between computing device 402 and other devices (e.g. user computing device 330 and sequencing system 310, shown in FIG. 1) over a network, such as network 350 (shown in FIG. 1), or a plurality of network connections using predefined network protocols such as TCP/IP (Transmission Control Protocol/Internet Protocol).

Figure 3:
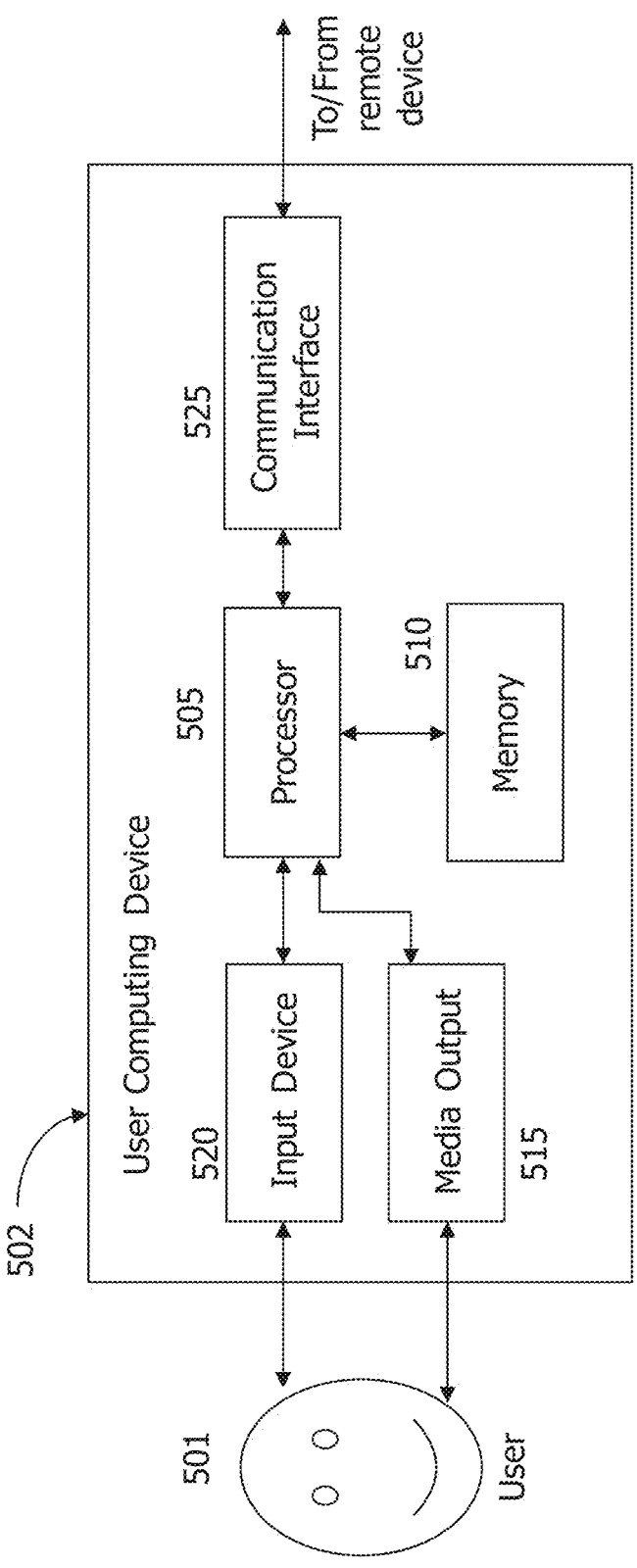
FIG. 3 is a block diagram schematically illustrating a remote or user computing device in accordance with one aspect of the disclosure.

FIG. 3 depicts a configuration of a remote or user-computing device 502, such as user computing device 330 (shown in FIG. 1). Computing device 502 may include a processor 505 for executing instructions. In some aspects, executable instructions may be stored in a memory area 510. Processor 505 may include one or more processing units (e.g., in a multi-core configuration). Memory area 510 may be any device allowing information such as executable instructions and/or other data to be stored and retrieved. Memory area 510 may include one or more computer-readable media.

Computing device 502 may also include at least one media output component 515 for presenting information to a user 501. Media output component 515 may be any component capable of conveying information to user 501. In some aspects, media output component 515 may include an output adapter, such as a video adapter and/or an audio adapter. An output adapter may be operatively coupled to processor 505 and operatively coupleable to an output device such as a display device (e.g., a liquid crystal display (LCD), organic light emitting diode (OLED) display, cathode ray tube (CRT), or "electronic ink" display) or an audio output device (e.g., a speaker or headphones). In some aspects, media output component 515 may be configured to present an interactive user interface (e.g., a web browser or client application) to user 501.

In some aspects, computing device 502 may include an input device 520 for receiving input from user 501. Input device 520 may include, for example, a keyboard, a pointing device, a mouse, a stylus, a touch-sensitive panel (e.g., a touchpad or a touch screen), a camera, a gyroscope, an accelerometer, a position detector, and/or an audio input device. A single component such as a touch screen may function as both an output device of media output component 515 and input device 520.

Computing device 502 may also include a communication interface 525, which may be communicatively coupleable to a remote device. Communication interface 525 may include, for example, a wired or wireless network adapter or a wireless data transceiver for use with a mobile phone network (e.g., Global System for Mobile communications (GSM), 3G, 4G, or Bluetooth) or other mobile data network (e.g., Worldwide Interoperability for Microwave Access (WIMAX)).

Stored in memory area 510 are, for example, computer-readable instructions for providing a user interface to user 501 via media output component 515 and, optionally, receiving and processing input from input device 520. A user interface may include, among other possibilities, a web browser and client application. Web browsers enable users 501 to display and interact with media and other information typically embedded on a web page or a website from a web server. A client application allows users 501 to interact with a server application associated with, for example, a vendor or business.

Figure 4:
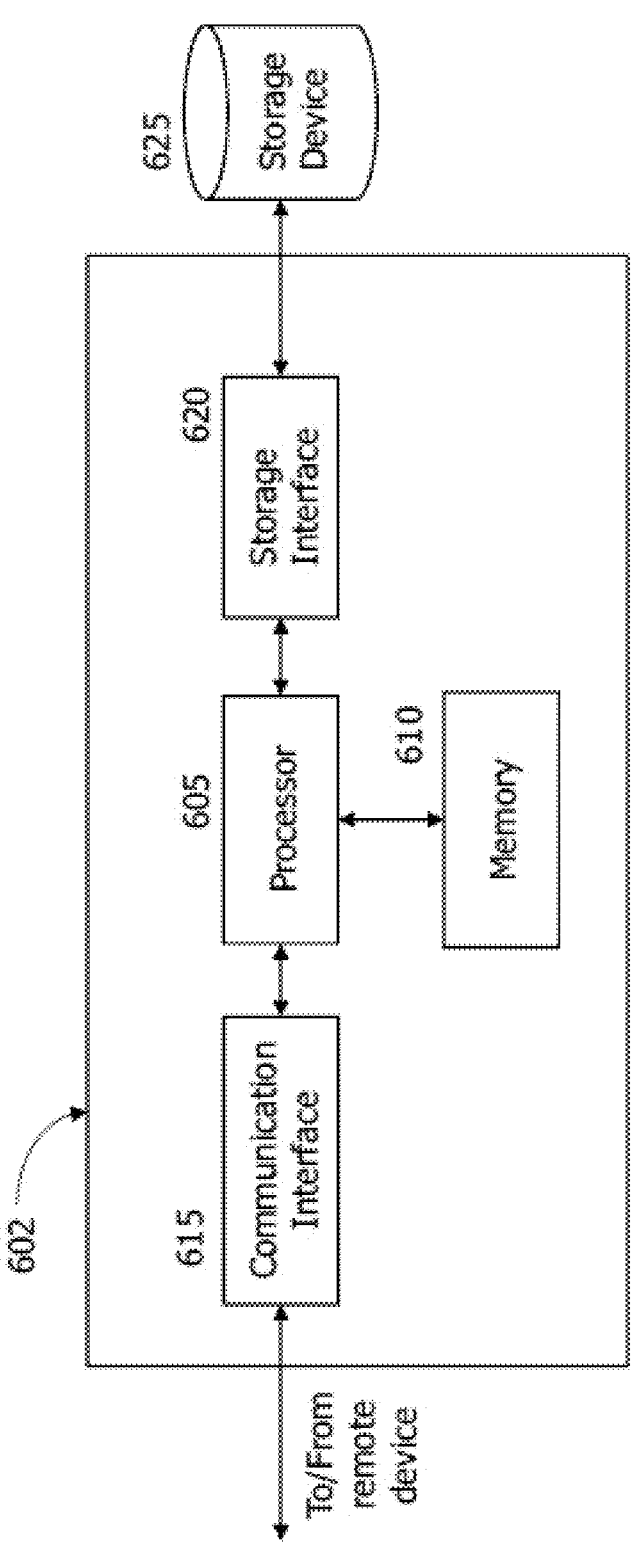
FIG. 4 is a block diagram schematically illustrating a server system in accordance with one aspect of the disclosure.

FIG. 4 illustrates an example configuration of a server system 602. Server system 602 may include, but is not limited to, database server 306 and computing device 302 (both shown in FIG. 1). In some aspects, server system 602 is similar to server system 304 (shown in FIG. 1). Server system 602 may include a processor 605 for executing instructions. Instructions may be stored in a memory area 625, for example. Processor 605 may include one or more processing units (e.g., in a multi-core configuration).

Processor 605 may be operatively coupled to a communication interface 615 such that server system 602 may be capable of communicating with a remote device such as user computing device 330 (shown in FIG. 1) or another server system 602. For example, communication interface 615 may receive requests from user computing device 330 via a network 350 (shown in FIG. 1).

Processor 605 may also be operatively coupled to a storage device 625. Storage device 625 may be any computer-operated hardware suitable for storing and/or retrieving data. In some aspects, storage device 625 may be integrated in server system 602. For example, server system 602 may include one or more hard disk drives as storage device 625. In other aspects, storage device 625 may be external to server system 602 and may be accessed by a plurality of server systems 602. For example, storage device 625 may include multiple storage units such as hard disks or solid-state disks in a redundant array of inexpensive disks (RAID) configuration. Storage device 625 may include a storage area network (SAN) and/or a network attached storage (NAS) system.

In some aspects, processor 605 may be operatively coupled to storage device 625 via a storage interface 620. Storage interface 620 may be any component capable of providing processor 605 with access to storage device 625. Storage interface 620 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 605 with access to storage device 625.

Memory areas 510 (shown in FIG. 3) and 610 may include, but are not limited to, random access memory (RAM) such as dynamic RAM (DRAM) or static RAM (SRAM), read-only memory (ROM), erasable programmable read-only memory (EPROM), electrically erasable programmable read-only memory (EEPROM), and non-volatile RAM (NVRAM). The above memory types are examples only, and are thus not limiting as to the types of memory usable for storage of a computer program.

The computer systems and computer-implemented methods discussed herein may include additional, less, or alternate actions and/or functionalities, including those discussed elsewhere herein. The computer systems may include or be implemented via computer-executable instructions stored on non-transitory computer-readable media. The methods may be implemented via one or more local or remote processors, transceivers, servers, and/or sensors (such as processors, transceivers, servers, and/or sensors mounted on vehicle or mobile devices, or associated with smart infrastructure or remote servers), and/or via computer executable instructions stored on non-transitory computer-readable media or medium.

In some aspects, a computing device is configured to implement machine learning, such that the computing device "learns" to analyze, organize, and/or process data without being explicitly programmed. Machine learning may be implemented through machine learning (ML) methods and algorithms. In one aspect, a machine learning (ML) module is configured to implement ML methods and algorithms. In some aspects, ML methods and algorithms are applied to data inputs and generate machine learning (ML) outputs. Data inputs may further include: sequencing data, sensor data, image data, video data, telematics data, authentication data, authorization data, security data, mobile device data, geolocation information, transaction data, personal identification data, financial data, usage data, weather pattern data, "big data" sets, and/or user preference data. In some aspects, data inputs may include certain ML outputs.

In some aspects, at least one of a plurality of ML methods and algorithms may be applied, which may include but are not limited to: linear or logistic regression, instance-based algorithms, regularization algorithms, decision trees, Bayesian networks, cluster analysis, association rule learning, artificial neural networks, deep learning, dimensionality reduction, and support vector machines. In various aspects, the implemented ML methods and algorithms are directed toward at least one of a plurality of categorizations of machine learning, such as supervised learning, unsupervised learning, and reinforcement learning.

In one aspect, ML methods and algorithms are directed toward supervised learning, which involves identifying patterns in existing data to make predictions about subsequently received data. Specifically, ML methods and algorithms directed toward supervised learning are "trained" through training data, which includes example inputs and associated example outputs. Based on the training data, the ML methods and algorithms may generate a predictive function that maps outputs to inputs and utilize the predictive function to generate ML outputs based on data inputs. The example inputs and example outputs of the training data may include any of the data inputs or ML outputs described above.

In another aspect, ML methods and algorithms are directed toward unsupervised learning, which involves finding meaningful relationships in unorganized data. Unlike supervised learning, unsupervised learning does not involve user-initiated training based on example inputs with associated outputs. Rather, in unsupervised learning, unlabeled data, which may be any combination of data inputs and/or ML outputs as described above, is organized according to an algorithm-determined relationship.

In yet another aspect, ML methods and algorithms are directed toward reinforcement learning, which involves optimizing outputs based on feedback from a reward signal. Specifically ML methods and algorithms directed toward reinforcement learning may receive a user-defined reward signal definition, receive a data input, utilize a decision-making model to generate an ML output based on the data input, receive a reward signal based on the reward signal definition and the ML output, and alter the decision-making model so as to receive a stronger reward signal for subsequently generated ML outputs. The reward signal definition may be based on any of the data inputs or ML outputs described above. In one aspect, an ML module implements reinforcement learning in a user recommendation application. The ML module may utilize a decision-making model to generate a ranked list of options based on user information received from the user and may further receive selection data based on a user selection of one of the ranked options. A reward signal may be generated based on comparing the selection data to the ranking of the selected option. The ML module may update the decision-making model such that subsequently generated rankings more accurately predict a user selection.

As will be appreciated based upon the foregoing specification, the above-described aspects of the disclosure may be implemented using computer programming or engineering techniques including computer software, firmware, hardware or any combination or subset thereof. Any such resulting program, having computer-readable code means, may be embodied or provided within one or more computer-readable media, thereby making a computer program product, i.e., an article of manufacture, according to the discussed aspects of the disclosure. The computer-readable media may be, for example, but is not limited to, a fixed (hard) drive, diskette, optical disk, magnetic tape, semiconductor memory such as read-only memory (ROM), and/or any transmitting/receiving medium, such as the Internet or other communication network or link. The article of manufacture containing the computer code may be made and/or used by executing the code directly from one medium, by copying the code from one medium to another medium, or by transmitting the code over a network.

These computer programs (also known as programs, software, software applications, "apps", or code) include machine instructions for a programmable processor and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The "machine-readable medium" and "computer-readable medium," however, do not include transitory signals. The term "machine-readable signal" refers to any signal used to provide machine instructions and/or data to a programmable processor.

As used herein, a processor may include any programmable system including systems using micro-controllers, reduced instruction set circuits (RISC), application specific integrated circuits (ASICs), logic circuits, and any other circuit or processor capable of executing the functions described herein. The above examples are examples only, and are thus not intended to limit in any way the definition and/or meaning of the term "processor."

As used herein, the terms "software" and "firmware" are interchangeable, and include any computer program stored in memory for execution by a processor, including RAM memory, ROM memory, EPROM memory, EEPROM memory, and non-volatile RAM (NVRAM) memory. The above memory types are examples only, and are thus not limiting as to the types of memory usable for storage of a computer program.

In one aspect, a computer program is provided, and the program is embodied on a computer-readable medium. In one aspect, the system is executed on a single computer system, without requiring a connection to a server computer. In a further aspect, the system is being run in a Windows® environment (Windows is a registered trademark of Microsoft Corporation, Redmond, Washington). In yet another aspect, the system is run on a mainframe environment and a UNIX® server environment (UNIX is a registered trademark of X/Open Company Limited located in Reading, Berkshire, United Kingdom). The application is flexible and designed to run in various different environments without compromising any major functionality.

In some aspects, the system includes multiple components distributed among a plurality of computing devices. One or more components may be in the form of computer-executable instructions embodied in a computer-readable medium. The systems and processes are not limited to the specific aspects described herein. In addition, components of each system and each process can be practiced independent and separate from other components and processes described herein. Each component and process can also be used in combination with other assembly packages and processes. The present aspects may enhance the functionality and functioning of computers and/or computer systems.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein. The recitation of discrete values is understood to include ranges between each value.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Any publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing from the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1—a Novel Oscillation Detection Method Considering 1/F Noise and Auto-Correlation of Neurophysiological Signal Detecting temporal and spectral features of neural oscillations is essential to understanding dynamic brain function. Traditionally, the presence and frequency of neural oscillations are determined by identifying peaks over 1/f noise within the power spectrum. However, this approach solely operates within the frequency domain and thus can neither accurately determine the oscillation's onset/offset time, nor properly distinguish between the fundamental frequency of a non-sinusoidal oscillation and its harmonics.

To overcome these limitations, a novel method to identify neural oscillations was developed based on three principle criteria: 1. Oscillations (peaks over 1/f noise) must be present in the time and frequency domain; 2. Oscillations must exhibit at least two full cycles; and 3. Oscillations must share the same periodicity as the original time-series auto-correlation.

Non-sinusoidal signals are known to generate harmonics, significantly increasing the false-positive detection rate—the confounding factor that is addressed by the third criterion in the method.

The method was evaluated by verifying its performance on simulated sinusoidal and non-sinusoidal oscillatory bursts convolved with 1/f noise. The results demonstrate that the method outperforms the conventional techniques in accurately detecting oscillations. The sensitivity of the method was also observed to be a function of signal-to-noise ratio (SNR) that is negatively influenced by sub-optimal SNR.

The method was further assessed by testing it on electrocorticographic (ECoG, N=8) and electroencephalographic (EEG, N=7) signals recorded during the pre-stimulus period of an auditory reaction time task. The method detected auditory alpha and pre-motor beta oscillations in ECoG signals; occipital alpha and pre-motor beta oscillations in EEG signals; and accurately determined the offset of these oscillations to correspond with the onset of the auditory stimuli.

In summary, the described method demonstrates high precision and specificity in detecting neural oscillations in time and frequency domains.

Example 2—Targeted Neurofeedback

The high specificity of the method of the present disclosure in detecting neural oscillations can improve the effectiveness of neurofeedback-based systems. For example, a neurofeedback system may provide targeted feedback on the magnitude of the user's alpha oscillation to improve attention to improve task performance. For this purpose, the system can detect the user's alpha oscillation with high specificity. High specificity requires distinguishing other oscillations and artifacts from true physiological alpha oscillations. The high specificity of the method of the present disclosure thus enables targeted neurofeedback applications to enhance or restore task performance.

Example 3—Phase-Locked Electrical Stimulation

Neuromodulation is most-effective when electrical stimulation is delivered phase-locked to the underlying ongoing oscillation. For example, deep-brain stimulation in phase with ongoing oscillation can reduce the amount of stimulation necessary to achieve the desired therapeutic effect. This reduced efficiency in delivering the stimulation therapy reduces power consumption and thus enhances the battery life of the implanted system. Longer battery life means fewer battery changes (which require surgical procedures), or for rechargeable systems, fewer recharging sessions (which require the user's attention). Realizing phase-locked neuromodulation requires detecting an ongoing oscillation with high specificity and delivering the electrical stimulation at a predicted phase of the oscillation. The high specificity of the method of the present disclosure thus enables neuromodulation applications that depend on phase-locked electrical stimulation.

What is claimed is:

1. A A computer-implemented method for the identification of oscillations within electromagnetic (EM) activity of a brain of a patient, the method implemented on a computing device comprising at least one processor in communication with at least one non-transitory computer readable medium, the method comprising:

a. receiving, at the computing device, a plurality of EM measurements indicative of EM activity of the brain and corresponding times;

b. transforming, using the computing device, the plurality of EM measurements into a three-dimensional time-frequency space;

c. removing aperiodic activity to perform a first filtering on the plurality of EM measurements in the three-dimensional time-frequency space using the computing device, wherein the time-frequency space includes a plurality of frequency points, wherein the first filtering removes EM measurements of the plurality of EM measurements containing pink noise to generate a flattened three-dimensional time-frequency space by providing thresholds within the time-frequency space to identify periodic signals for each frequency point of the plurality of frequency points;

d. constructing, using the computing device, a first plurality of bounding boxes, each bounding box of the first plurality of bounding boxes enclosing a contiguous group of the EM measurements of the plurality of EM measurements to capture onset and offset times of candidate oscillations within the flattened three-dimensional time-frequency space, wherein the contiguous group of the EM measurements of the plurality of EM measurements are detected where spectral power is above the thresholds within the time-frequency space;

e. performing a second filtering, using the computing device, on the first plurality of bounding boxes to reject bounding boxes of the plurality of bounding boxes enclosing less than two candidate oscillation cycles to generate a second plurality of bounding boxes, wherein candidate oscillations are detected based on detecting harmonic peaks in a corresponding bounding box of the plurality of bounding boxes;

f. performing, using the computing device, an autocorrelation on the EM measurements of the plurality of EM measurements within each bounding box of the second plurality of bounding boxes to identify a corresponding frequency for each corresponding bounding box of the second plurality of bounding boxes by analyzing intervals of peaks and troughs of the candidate oscillations in the corresponding bounding box to identify the corresponding frequency for the corresponding bounding box;

g. performing a third filtering, using the computing device, on the second plurality of bounding boxes to retain only the bounding boxes of the second plurality of bounding boxes containing candidate oscillations with corresponding frequencies equal to a center frequency of the candidate oscillations to generate a third plurality of bounding boxes, wherein the center frequency is calculated as a center of frequencies of a plurality of EM signals in the corresponding bounding box;

h. displaying, using the computing device, the candidate oscillations in the third plurality of bounding boxes to a user; and i. providing, based on the candidate oscillations, at least one of (1) targeted neurofeedback to the patient, (2) phase-locked neuromodulation to the patient, or (3) therapeutic treatment to the patient.

2. The computer-implemented method of claim 1, further comprising determining for each candidate oscillation the onset time, the offset time, the center frequency, a frequency range, a number of cycles, and a degree of asymmetry.

3. The computer-implemented method of claim 1, wherein the candidate oscillations include rhythmic, repeating patterns of neural activity including at least one of delta, theta, alpha, beta, and low gamma band oscillations.

4. The computer-implemented method of claim 1, wherein the second plurality of bounding boxes with at least two candidate oscillation cycles represent event-related potentials and evoked responses from a group of neurons by an external stimulus or event.

5. The computer-implemented method of claim 1, further comprising grouping the candidate oscillations by frequency range to generate a normalized power map.

6. The computer-implemented method of claim 1, further comprising incorporating at least one of a brain-computer interface and a neurofeedback system.

7. The computer-implemented method of claim 1, wherein the plurality of EM measurements include at least one of electroencephalography (EEG) signals, magnetoencephalography (MEG) signals, electrocorticography (ECOG) signals, stereo EEG (SEEG) signals, single neuronal recordings, and local field potentials (LFP).

8. A system for identifying oscillations within electromagnetic (EM) activity of a brain of a patient, the system comprising at least one processor in communication with at least one memory device, wherein the at least one processor is configured to:

a. receive a plurality of EM measurements indicative of EM activity of the brain and corresponding times;

b. transform the plurality of EM measurements into a three-dimensional time-frequency space;

c. remove aperiodic activity to perform a first filtering on the plurality of EM measurements in the three-dimensional time-frequency space, wherein the time-frequency space includes a plurality of frequency points, wherein the first filtering remove EM measurements of the plurality of EM measurements containing pink noise to generate a three-dimensional flattened time-frequency space by providing thresholds within the time-frequency space to identify periodic signals for each frequency point of the plurality of frequency points;

d. construct a first plurality of bounding boxes, each bounding box of the first plurality of bounding boxes enclosing a contiguous group of the EM measurements of the plurality of EM measurements to capture onset and offset times of candidate oscillations within the flattened three-dimensional time-frequency space, wherein the contiguous group of the EM measurements of the plurality of EM measurements are detected where spectral power is above the thresholds within the time-frequency space;

e. perform a second filtering on the first plurality of bounding boxes to reject bounding boxes of the first plurality of bounding boxes enclosing less than two candidate oscillation cycles to generate a second plurality of bounding boxes, wherein candidate oscillations are detected based on detecting harmonic peaks in a corresponding bounding box of the plurality of bounding boxes;

f. perform an autocorrelation on the EM measurements of the plurality of EM measurements within each bounding box of the second plurality of bounding boxes to identify a corresponding frequency for each corresponding bounding box of the second plurality of bounding boxes by analyzing intervals of peaks and troughs of the candidate oscillations in the corresponding bounding box to identify the corresponding frequency for the corresponding bounding box;

g. perform a third filtering of the second plurality of bounding boxes to retain only the bounding boxes of the second plurality of bounding boxes containing candidate oscillations with corresponding frequencies equal to a center frequency of the candidate oscillations to generate a third plurality of bounding boxes, wherein the center frequency is calculated as a center of frequencies of a plurality of EM signals in the corresponding bounding box;

h. communicate the candidate oscillations in the third plurality of bounding boxes to a user; and i. provide, based on the candidate oscillations, at least one of (1) targeted neurofeedback to the patient, (2) phase-locked neuromodulation to the patient, or (3) therapeutic treatment to the patient.

9. The system of claim 8, wherein the at least one processor is further configured to determine for each candidate oscillation the onset time, the offset time, the center frequency, a frequency range, a number of cycles, and a degree of asymmetry.

10. The system of claim 8, wherein the candidate oscillations include rhythmic, repeating patterns of neural activity including at least one of delta, theta, alpha, beta, and low gamma band oscillations.

11. The system of claim 8, wherein the second plurality of bounding boxes with at least two candidate oscillation cycles represent event-related potentials and evoked responses from a group of neurons by an external stimulus or event.

12. The system of claim 8, wherein the at least one processor is further configured to group candidate oscillations by frequency range to generate a normalized power map.

13. The system of claim 8, wherein the at least one processor is further configured to incorporate at least one of a brain-computer interface and a neurofeedback system.

14. The system of claim 8, wherein the plurality of EM measurements include at least one of electroencephalography (EEG) signals, magnetoencephalography (MEG) signals, electrocorticography (ECoG) signals, stereo EEG (sEEG) signals, single neuronal recordings, and local field potentials (LFP).

15. The system of claim 8, wherein the at least one processor is further configured to use the candidate oscillations in the third plurality of bounding boxes to provide targeted feedback on a magnitude of a user's alpha oscillation to improve attention and improve task performance.

16. The system of claim 8, wherein the at least one processor is further configured to adjust a phase of electrical stimulation based on the candidate oscillations in the third plurality of bounding boxes.

17. At least one non-transitory computer-readable media having computer-executable instructions embodied thereon, when executed by a computing device including at least one processor in communication with at least one memory device, the computer-executable instructions cause the at least one processor to:

a. receive a plurality of EM measurements indicative of EM activity of a brain of a patient and corresponding times;

b. transform the plurality of EM measurements into a three-dimensional time-frequency space;

c. remove aperiodic activity to perform a first filtering on the plurality of EM measurements in the three-dimensional time-frequency space, wherein the time-frequency space includes a plurality of frequency points, wherein the first filtering remove EM measurements of the plurality of EM measurements containing pink noise to generate a three-dimensional flattened time-frequency space by providing thresholds within the time-frequency space to identify periodic signals for each frequency point of the plurality of frequency points;

d. construct a first plurality of bounding boxes, each bounding box of the first plurality of bounding boxes enclosing a contiguous group of the EM measurements of the plurality of EM measurements to capture onset and offset times of candidate oscillations within the flattened three-dimensional time-frequency space, wherein the contiguous group of the EM measurements of the plurality of EM measurements are detected where spectral power is above the thresholds within the time-frequency space;

e. perform a second filtering on the first plurality of bounding boxes to reject bounding boxes of the first plurality of bounding boxes enclosing less than two candidate oscillation cycles to generate a second plurality of bounding boxes, wherein candidate oscillations are detected based on detecting harmonic peaks in a corresponding bounding box of the plurality of bounding boxes;

f. perform an autocorrelation on the EM measurements of the plurality of EM measurements within each bounding box of the second plurality of bounding boxes to identify a corresponding frequency for each corresponding bounding box of the second plurality of bounding boxes by analyzing intervals of peaks and troughs of the candidate oscillations in the corresponding bounding box to identify the corresponding frequency for the corresponding bounding box;

g. perform a third filtering of the second plurality of bounding boxes to retain only the bounding boxes of the second plurality of bounding boxes containing candidate oscillations with corresponding frequencies equal to a center frequency of the candidate oscillations to generate a third plurality of bounding boxes, wherein the center frequency is calculated as a center of frequencies of a plurality of EM signals in the corresponding bounding box;

h. communicate the candidate oscillations in the third plurality of bounding boxes to a user; and i. provide, based on the candidate oscillations, at least one of (1) targeted neurofeedback to the patient, (2) phase-locked neuromodulation to the patient, or (3) therapeutic treatment to the patient.

18. The at least one non-transitory computer-readable media of claim 17, wherein the computer-executable instructions cause the at least one processor to determine for each candidate oscillation the onset time, the offset time, the center frequency, a frequency range, a number of cycles, and a degree of asymmetry.

19. The at least one non-transitory computer-readable media of claim 17, wherein the candidate oscillations include rhythmic, repeating patterns of neural activity including at least one of delta, theta, alpha, beta, and low gamma band oscillations.

20. The at least one non-transitory computer-readable media of claim 17, wherein the second plurality of bounding boxes with at least two candidate oscillation cycles represent event-related potentials and evoked responses from a group
of neurons by an external stimulus or event.

* * * * *